US010292652B2

(12) United States Patent
Berg et al.

(10) Patent No.: US 10,292,652 B2
(45) Date of Patent: May 21, 2019

(54) SYSTEM AND METHOD FOR MONITORING BIOMETRIC SIGNALS

(71) Applicant: Mad Apparel, Inc., Redwood City, CA (US)

(72) Inventors: James Berg, San Francisco, CA (US); Hamid Butt, Cupertino, CA (US); Dhananja Jayalath, Redwood City, CA (US); Christopher Wiebe, Burlingame, CA (US)

(73) Assignee: MAD APPAREL, INC., Redwood City, CA (US)

( * ) Notice: Subject to any disclaimer, the term of this patent is extended or adjusted under 35 U.S.C. 154(b) by 211 days.

(21) Appl. No.: 14/541,446

(22) Filed: Nov. 14, 2014

(65) Prior Publication Data

US 2015/0148619 A1   May 28, 2015

Related U.S. Application Data

(60) Provisional application No. 61/908,077, filed on Nov. 23, 2013, provisional application No. 62/013,405, (Continued)

(51) Int. Cl.
*A61B 5/11* (2006.01)
*A61B 5/00* (2006.01)
(Continued)

(52) U.S. Cl.
CPC .......... *A61B 5/6804* (2013.01); *A61B 5/0024* (2013.01); *A61B 5/1112* (2013.01);
(Continued)

(58) Field of Classification Search
CPC ........................... A61B 5/6804; A61B 5/0024
(Continued)

(56) References Cited

U.S. PATENT DOCUMENTS 3,534,727 A   10/1970 Roman
3,973,099 A    8/1976 Morris
(Continued)

FOREIGN PATENT DOCUMENTS

KR   2014 0008971 A   1/2014
WO   WO 01/15286 A1   3/2001
(Continued)

OTHER PUBLICATIONS

StudSeal press release, Douglas Electrical Components, http://news.thomasnet.com/fullstory/hermetic-feedthroughs-suit-high-current-applications-827050, May 21, 2009.*
(Continued)

*Primary Examiner* — Carl H Layno
*Assistant Examiner* — Dacheng Xie
(74) *Attorney, Agent, or Firm* — Fenwick & West LLP

(57) ABSTRACT

A system for monitoring biometric signals of a user comprising: a garment configured to be worn by the user and comprising a mounting module having an array of connection regions; a set of biometric sensors coupled to the garment and configured to communicate with the array of connection regions to receive and transmit biometric signals indicative of muscle activity of the user; and a portable control module configured to couple to the garment in a first configuration and to decouple from the garment in a second configuration and comprising: a housing comprising an array of openings; a set of contacts, each including a first region that hermetically seals at least one of the array of openings and couples to at least one of the array of connection regions in the first configuration, and an electronics subsystem coupled to the housing and in communication with a second region of each contact.

23 Claims, 12 Drawing Sheets

Related U.S. Application Data filed on Jun. 17, 2014, provisional application No. 62/016,373, filed on Jun. 24, 2014, provisional application No. 62/077,781, filed on Nov. 10, 2014.

(51) Int. Cl.

| | |
|---|---|
| A61B 5/0492 | (2006.01) |
| A61B 5/0205 | (2006.01) |
| A61B 5/0408 | (2006.01) |
| A61B 5/0478 | (2006.01) |
| A61B 5/0496 | (2006.01) |
| A61B 5/053 | (2006.01) |
| A61B 5/024 | (2006.01) |
| A61B 5/08 | (2006.01) |

(52) U.S. Cl.
CPC ............ *A61B 5/1118* (2013.01); *A61B 5/024* (2013.01); *A61B 5/0205* (2013.01); *A61B 5/0408* (2013.01); *A61B 5/0478* (2013.01); *A61B 5/0492* (2013.01); *A61B 5/0496* (2013.01); *A61B 5/0533* (2013.01); *A61B 5/08* (2013.01); *A61B 5/7445* (2013.01); *A61B 2505/09* (2013.01)

(58) Field of Classification Search
USPC .................................................. 600/300–301
See application file for complete search history.

(56) References Cited

U.S. PATENT DOCUMENTS

| | | | |
|---|---|---|---|
| 3,982,529 | A | 9/1976 | Sato |
| 4,400,341 | A | 8/1983 | Sorensen |
| 4,706,680 | A | 11/1987 | Keusch et al. |
| 4,729,377 | A | 3/1988 | Granek et al. |
| 4,799,441 | A | 1/1989 | Boser |
| 6,002,957 | A | 12/1999 | Finneran |
| 6,350,129 | B1 | 2/2002 | Gorlick |
| 6,381,482 | B1 † | 4/2002 | Jayaraman |
| 6,970,731 | B1 † | 11/2005 | Jayaraman |
| 6,978,684 | B2 | 12/2005 | Nurse |
| 7,152,470 | B2 † | 12/2006 | Impio |
| 7,173,437 | B2 | 2/2007 | Hervieux et al. |
| 7,308,294 | B2 † | 12/2007 | Hassonjee |
| 7,474,910 | B2 | 1/2009 | Hassonjee et al. |
| 7,559,902 | B2 | 7/2009 | Ting et al. |
| 7,602,301 | B1 | 10/2009 | Stirling et al. |
| 7,783,334 | B2 | 8/2010 | Nam et al. |
| 7,821,407 | B2 | 10/2010 | Shears et al. |
| 7,825,815 | B2 | 11/2010 | Shears et al. |
| 7,978,081 | B2 | 7/2011 | Shears et al. |
| 8,006,633 | B2 | 8/2011 | Bennett et al. |
| 8,032,199 | B2 | 10/2011 | Linti et al. |
| 8,146,171 | B2 | 4/2012 | Chung et al. |
| 8,214,007 | B2 | 7/2012 | Baker et al. |
| 8,267,701 | B2 | 9/2012 | Beaman et al. |
| 8,280,503 | B2 | 10/2012 | Linderman |
| 8,475,371 | B2 | 7/2013 | Derchak et al. |
| 8,560,044 | B2 | 10/2013 | Kurzweil et al. |
| 8,750,959 | B2 | 6/2014 | Lindberg et al. |
| 8,798,708 | B2 | 8/2014 | Tremblay |
| 8,818,478 | B2 | 8/2014 | Scheffler et al. |
| 8,821,305 | B2 | 9/2014 | Cusey et al. |
| 8,909,318 | B2 | 12/2014 | Nordstrom |
| 2004/0187184 | A1 | 9/2004 | Rubin et al. |
| 2004/0254624 | A1 | 12/2004 | Johnson |
| 2005/0177059 | A1 | 8/2005 | Koivumaa et al. |
| 2005/0178201 | A1* | 8/2005 | Impio .................. A61B 5/0488 73/379.01 |
| 2006/0264730 | A1 | 11/2006 | Stivoric et al. |
| 2007/0038057 | A1 | 2/2007 | Nam et al. |
| 2007/0285868 | A1 | 12/2007 | Lindberg et al. |
| 2008/0092341 | A1 | 4/2008 | Ahmadshahi |
| 2008/0096726 | A1 | 4/2008 | Riley et al. |
| 2008/0278899 | A1* | 11/2008 | Hotelling ............ G06F 1/1632 361/679.41 |
| 2008/0288026 | A1* | 11/2008 | Cross .................. A61B 5/0408 607/60 |
| 2009/0012408 | A1 | 1/2009 | Nagata et al. |
| 2009/0024017 | A1 | 1/2009 | Ruffini et al. |
| 2009/0270689 | A1* | 10/2009 | Galland ............... A61B 5/0002 600/300 |
| 2010/0037489 | A1* | 2/2010 | Berner, Jr. ........... A43B 3/0005 36/136 |
| 2010/0041974 | A1 | 2/2010 | Ting et al. |
| 2010/0117837 | A1 | 5/2010 | Stirling et al. |
| 2010/0185398 | A1 | 7/2010 | Berns et al. |
| 2010/0204616 | A1 | 8/2010 | Shears et al. |
| 2010/0234715 | A1 | 9/2010 | Shin et al. |
| 2010/0251454 | A1 | 10/2010 | Kiernan |
| 2010/0324405 | A1 | 12/2010 | Niemi et al. |
| 2011/0015498 | A1* | 1/2011 | Mestrovic ................ A61B 5/01 600/301 |
| 2011/0257546 | A1 | 10/2011 | Gozzini et al. |
| 2011/0288605 | A1 | 11/2011 | Kaib et al. |
| 2012/0068759 | A1 | 3/2012 | Clark et al. |
| 2012/0165645 | A1 | 6/2012 | Russell et al. |
| 2012/0208156 | A1 | 8/2012 | Rocklin |
| 2012/0330126 | A1 | 12/2012 | Hoppe et al. |
| 2013/0077263 | A1 | 3/2013 | Oleson et al. |
| 2013/0137943 | A1 | 5/2013 | Rodrigues |
| 2013/0137956 | A1 | 5/2013 | Okuda et al. |
| 2013/0172722 | A1 | 7/2013 | Ninane et al. |
| 2013/0192071 | A1 | 8/2013 | Esposito et al. |
| 2013/0198867 | A1* | 8/2013 | Ricci .................. G06F 13/4081 726/29 |
| 2013/0245388 | A1 | 9/2013 | Rafferty et al. |
| 2013/0324368 | A1 | 12/2013 | Aragones et al. |
| 2014/0070949 | A1 | 3/2014 | Chen |
| 2014/0070957 | A1* | 3/2014 | Longinotti-Buitoni ...................... A61B 5/02055 340/870.01 |
| 2014/0097944 | A1 | 4/2014 | Fastert et al. |
| 2014/0135593 | A1 | 5/2014 | Jayalth et al. |
| 2014/0172134 | A1 | 6/2014 | Meschter |
| 2014/0180023 | A1 | 6/2014 | Stivoric et al. |
| 2014/0189928 | A1 | 7/2014 | Oleson et al. |
| 2014/0275888 | A1 | 9/2014 | Wegerich et al. |
| 2014/0278125 | A1 | 9/2014 | Balakrishnan et al. |
| 2014/0296651 | A1 | 10/2014 | Stone |
| 2014/0343391 | A1 | 11/2014 | Korkala et al. |
| 2014/0352023 | A1 | 12/2014 | Mordecai et al. |
| 2015/0047091 | A1 | 2/2015 | Fournier et al. |
| 2015/0148619 | A1 | 5/2015 | Berg et al. |
| 2015/0181692 | A1 | 6/2015 | Jezewski et al. |
| 2016/0113581 | A1 † | 4/2016 | Amir |

FOREIGN PATENT DOCUMENTS

| | | |
|---|---|---|
| WO | 2006119345 A2 | 11/2006 |
| WO | WO 2007/063436 A1 | 6/2007 |

OTHER PUBLICATIONS

PCT International Search Report and Written Opinion, PCT Application No. PCT/US15/52969, dated Dec. 29, 2015, 11 pages.
European Extended Search Report, European Application No. 15847342.1, dated Mar. 13, 2018, 8 pages.
European Extended Search Report, European Application No. 15809222.1, dated Mar. 29, 2018, 9 pages.
PCT International Search Report and Written Opinion, PCT Application No. PCT/US2015/028900, dated Jul. 30, 2015, 12 pages.
United States Office Action, U.S. Appl. No. 14/702,129, dated Jul. 13, 2018, 11 pages.

\* cited by examiner
† cited by third party

CROSS SECTION

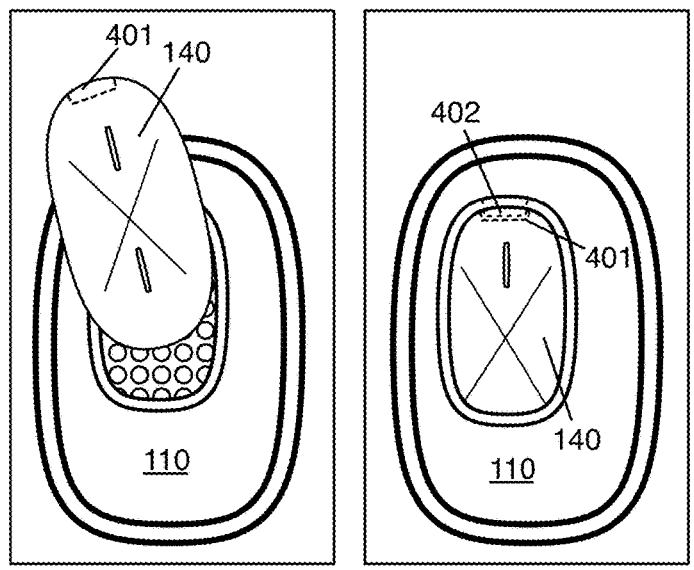
FIGURE 8C
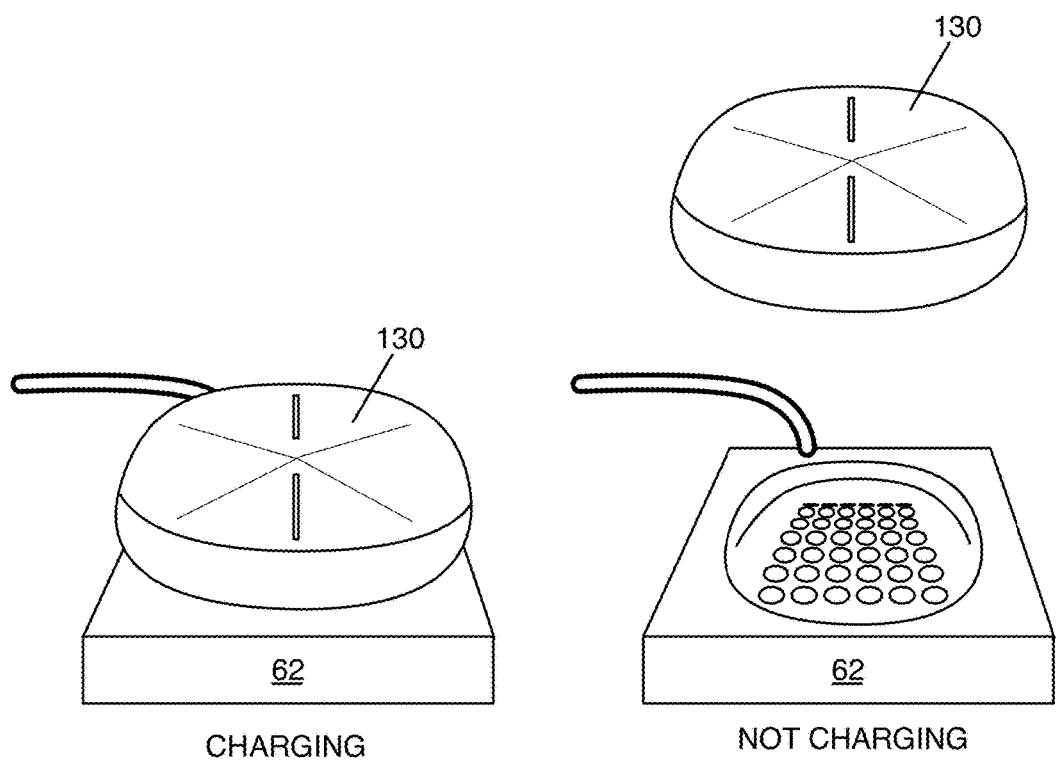
CHARGING
FIGURE 9A
NOT CHARGING
FIGURE 9B

EXAMPLE IMAGES FROM AN
EXERCISE-MONITORING APPLICATION

SYSTEM AND METHOD FOR MONITORING BIOMETRIC SIGNALS

CROSS-REFERENCE TO RELATED APPLICATIONS

This application claims the benefit of U.S. Provisional Application Ser. No. 61/908,077 filed 23 Nov. 2013, U.S. Provisional Application Ser. No. 62/013,405 filed 17 Jun. 2014, U.S. Provisional Application Ser. No. 62/016,373 filed 24 Jun. 2014, and U.S. Provisional Application Ser. No. 62/077,781 filed 10 Nov. 2014, which are each incorporated in its entirety herein by this reference.

TECHNICAL FIELD

This invention relates generally to the biometric device field, and more specifically to a new and useful system and method for monitoring biometric signals.

BACKGROUND

Tracking biometric parameters resulting from periods of physical activity can provide profound insights into improving one's performance and overall health. Historically, users have tracked their exercise behavior by manually maintaining records of aspects of their physical activity, including time points, durations, and/or other metrics (e.g., weight lifted, distance traveled, repetitions, sets, etc.) of their exercise behavior. Exercise tracking systems and software have been recently developed to provide some amount of assistance to a user interested in tracking his/her exercise behavior; however, such systems and methods still suffer from a number of drawbacks. In particular, many systems require a significant amount of effort from the user (e.g., systems rely upon user input prior to and/or after a period of physical activity), capture insufficient data (e.g., pedometers that estimate distance traveled, but provide little insight into an amount of physical exertion of the user), provide irrelevant information to a user, and are incapable of detecting body-responses to physical activity at a resolution sufficient to provide the user with a high degree of body awareness. Other limitations of conventional biometric monitoring devices include one or more of: involvement of single-use electrodes, involvement of a single electrode targeting a single body location, use of adhesives for electrode placement, contributions to user discomfort, and other deficiencies.

There is thus a need in the biometric device field to create a new and useful system and method for monitoring biometric signals. This invention provides such a new and useful system and method.

BRIEF DESCRIPTION OF THE FIGURES

FIG. 8C depicts a variation of a configuration between portions of a system for monitoring biometric signals of a user;

FIGS. 9A-9B depict configurations of charging modules in an example of a system for monitoring biometric signals of a user;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
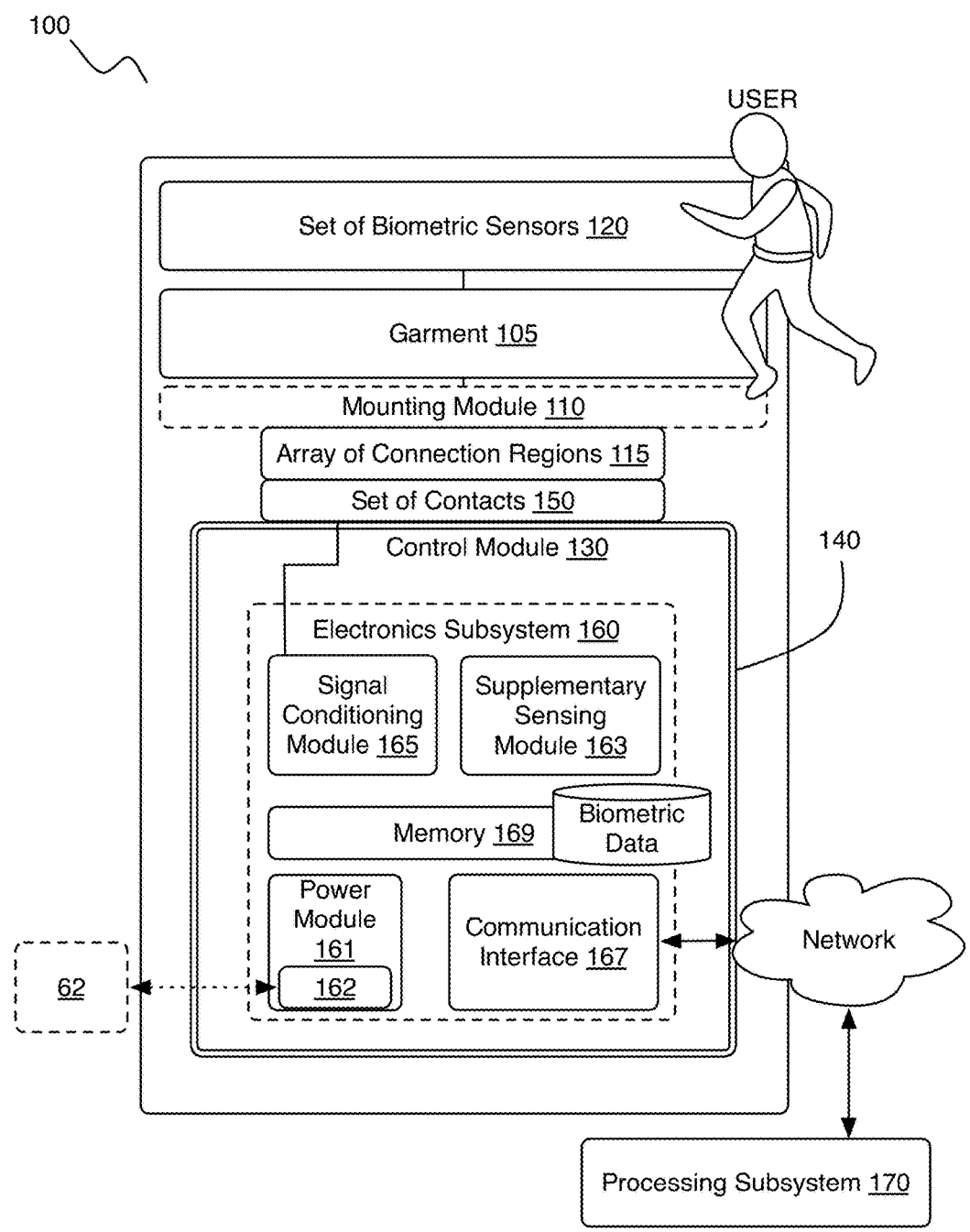
FIG. 1 depicts an embodiment of a system for monitoring biometric signals of a user.
Figure 2:
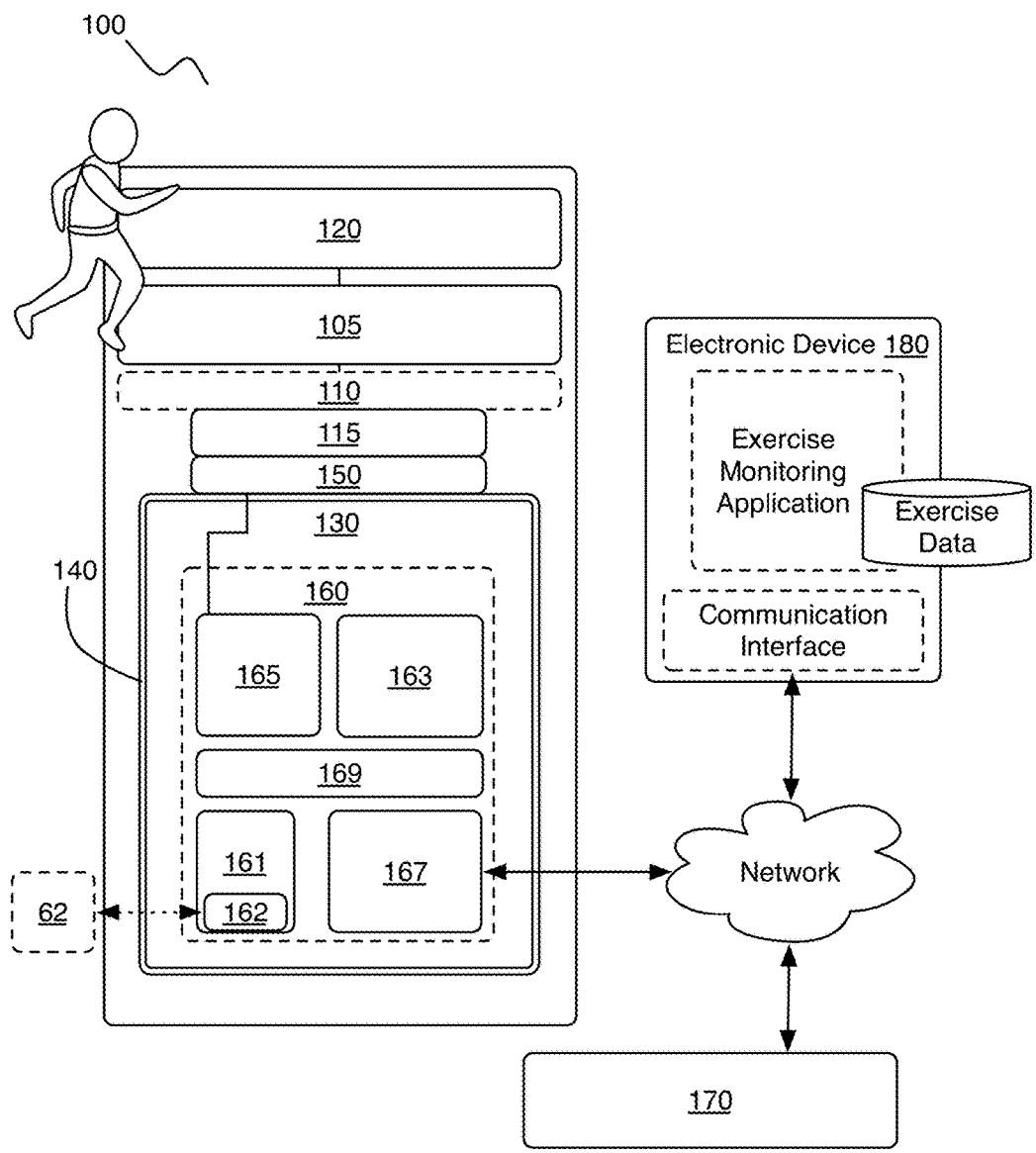
FIG. 2 depicts an embodiment of a system for monitoring biometric signals of a user, in communication with an external electronic device.

As shown in FIGS. 1 and 2, an embodiment of a system 100 for monitoring biometric signals of a user comprises: a garment 105; a set of biometric sensors 120 coupled to the garment and configured to receive biometric signals indicative of muscle activity of the user; and a control module 130 comprising a housing 140, a set of contacts 150 configured to couple to an array of connection regions 115 that enable signal transmission from the set of biometric sensors, and an electronics subsystem 160 in communication with the set of contacts. In some embodiments, the system 100 can further comprise one or more of: a mounting module no coupled to the garment and providing the array of connection regions; and a processing subsystem 170 configured to communicate with the electronics subsystem 160 and generate analyses based upon biometric signals detected by way of the set of biometric sensors.

The system 100 functions to position a set of biometric sensors at desired regions of a user's body, in order to detect biometric signals generated during physical activity of the user. The system 100 also functions to process detected biometric signals and to provide information derived from the processed biometric signals to the user performing a physical activity in substantially near real time, such that the user can gain insights into how to maintain or improve performance of the physical activity in a beneficial manner. In variations, the system 100 is configured to detect and process bioelectrical signals generated at a set of regions of the body of a user who is exercising (e.g., performing aerobic exercise, performing anaerobic exercise), and to present analyses in a visual manner (e.g., graphic manner, textual manner) by way of an application executing at an electronic device having a display. As such, bioelectrical signals detectable, processable, and/or analyzable by the system 100 can include any one or more of: electromyograph (EMG) signals, electrocardiography (ECG) signals, electroencephalograph (EEG) signals, magnetoencephalograph (MEG) signals, galvanic skin response (GSR) signals, electrooculograph (EOG) signals, and any other suitable bioelectrical signal of the user. The system 100 can, however, be configured to detect, process, and/or analyze any other suitable biosignal data of the user, including one or more of: heart rate data, movement data, respiration data, location data, environmental data (e.g., temperature data, light data, etc.), and any other suitable data.

In one embodiment, the system 100 can be configured to aggregate a combination of one or more of the biometric factors described above, and to determine and output a variety of metrics associated with the user's exercise activity. These metrics can provide the user with insights pertaining to his/her muscle exertion, muscle balance, exercise form, potential to incur injuries (e.g., acute injuries, chronic injuries), muscle fatigue, activity levels, muscle recovery behavior, exercise regimen parameters (e.g., types of exercise, sets of an exercise, repetitions of an exercise, etc.), and/or any other suitable exercise- or health-related factor.

The system 100 is preferably configured to be used by a user who is away from a research or clinical setting, such that the user is interfacing with a portion of the system 100 while he or she undergoes periods of activity in a natural setting (e.g., at a gym, outdoors, etc.). The system 100 can additionally or alternatively be configured to be operated by a user who is in a research setting, a clinical setting, or any other suitable setting. The system 100 is preferably configured to perform at least a portion of the method 200 described in Section 2 below; however, the system 100 can additionally or alternatively be configured to perform any other suitable method.

The garment 105 functions to position a set of biometric sensors proximal a set of body regions of the user, in order to enable detection of biometric signals from specific body regions of the user as the user is performing a form of physical exercise. The garment 105 can thus provide a means for providing close coupling and/or consistent placement of the set of biometric sensors at the body of the user. As such, the garment can be a form-fitting garment that provides a biasing force on the set of biometric sensors 120 described below, in order to promote close coupling between the set of biometric sensors 120 and desired portions of the body of the user. The garment can thus include a stretchable and/or compressive fabric comprising natural and/or synthetic fibers (e.g., nylon, lycra, polyester, spandex, etc.) to promote coupling (i.e., electrical coupling, mechanical coupling) and/or reduce motion artifacts that could otherwise result from relative motion between the skin of the user and the sensors of the set of biometric sensors 120. In examples, the garment 105 can include any one or more of: a top (e.g., shirt, jacket, tank top, etc.), bottom (e.g., shorts, pants, etc.), elbow pad, knee pad, arm sleeve, leg sleeve, socks, undergarment, neck wrap, glove, and any other suitable wearable garment. In some embodiments, the system 100 can comprise an embodiment of the garment described in U.S. application Ser. No. 14/079,629 entitled "Wearable Architecture and Methods for Performance Monitoring, Analysis, and Feedback" and filed on 13 Nov. 2013, which is herein incorporated in its entirety by this reference. However, the system 100 can alternatively comprise any other suitable garment.

Figure 3A:
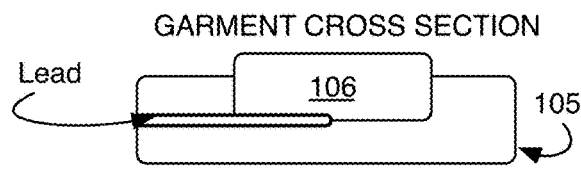
FIG. 3A depicts a cross-section of a portion of an embodiment of a system for monitoring biometric signals of a user.

In providing close coupling between the set of biometric sensors, as described below, and the body of the user, the garment 105 preferably comprises a plurality of conductive regions 106, as shown in FIG. 3A, configured to contact the set of body regions of the user from which biometric signal detection is desired, when the garment is worn by the user. As such, the plurality of conductive regions 106 can facilitate biometric signal transduction to the set of biometric sensors 120 described below. Preferably, the plurality of conductive regions 106 includes volumes of a conductive material that is integrated into the garment, wherein the conductive material is flexible, has good fatigue resistance, and is biocompatible (e.g., does not induce an allergic response, does not promote harboring of bacteria, etc.). The plurality of conductive regions 106 preferably also provide direct interfaces with the skin of the user when the garment is worn by the user, in order to facilitate electrical coupling with low impedance. However, in alternative variations, the plurality of conductive regions 106 can alternatively not directly contact skin of the user, but be configured to electrically couple to the user by way of an electrical coupling medium (e.g., saline, sweat, electrolyte medium, etc.) transmitted by way of the garment 105 or the user. In variations, the plurality of conductive regions 106 can include a conductive resin or silicone material formed directly onto a surface of the garment 105 facing the skin of the user, when the garment 105 is worn by the user, in order to facilitate signal transduction from the user to the set of biometric sensors 120 of the system 100. However, the conductive material can alternatively comprise any other suitable material and/or be configured in any other suitable manner.

The set of biometric sensors 120 is preferably coupled to the garment and configured to receive biometric signals indicative of muscle activity of the user. As such, the set of biometric sensors 120 function to detect bioelectric potentials (i.e., biopotentials) from body regions of the user, which vary according to different states of activity of the user. The set of biometric sensors 120, as described above, are preferably incorporated with or otherwise coupled to the plurality of conductive regions 106 of the garment 105; however, the set of biometric sensors 120 can include one or more biometric sensors that are configured to couple to the user in any other suitable manner (e.g., without involvement of the garment 105, without involvement of a plurality of conductive regions 106 of the garment 105).

The set of biometric sensors 120 preferably include electromyography (EMG) electrodes configured to acquire biopotential signals resulting from muscle activity of the user. However, in some variations, the set of biometric sensors 120 can additionally or alternatively include any one or more of: respiration sensors (e.g., sensors that operate according to plethysmography), galvanic skin response (GSR) sensors, temperature sensors, accelerometers (e.g., single axis accelerometers, multi-axis accelerometers), gyroscopes (e.g., single axis gyroscopes, multi-axis gyroscopes) global positioning system (GPS) sensors, vibration sensors, bioimpedance sensors, bend-angle measurement sensors, electrocardiography (ECG) sensors, sensors indicative of other cardiovascular parameters (e.g., pulse oximetry sensors, blood pressure sensors), and any other suitable type of sensor. As such, the set of biometric sensors 120 can detect biosignals indicative of one or multiple types of biological/physiological responses to activity of a user, in providing information relevant to exercise behavior of the user.

Figure 3B:
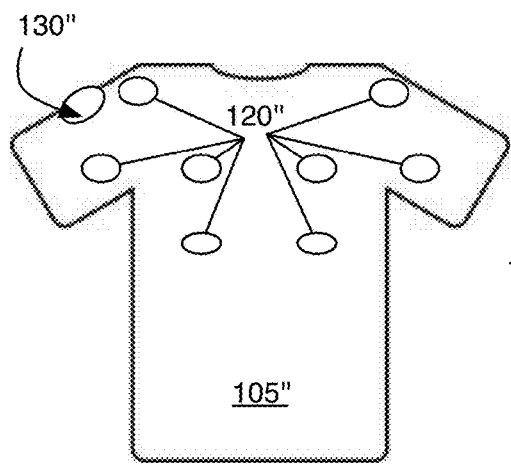
FIGS. 3B-3C depict different variations of garments in an embodiment of a system for monitoring biometric signals of a user.

Preferably, the type, number, and positioning of the set of biometric sensors is dependent upon the type(s) of garment(s) 105 included in the system 100. Additionally, for anatomical regions having contralateral pairs, the set of biometric sensors 120 preferably includes pairs of sensors, each pair including a first sensor at a first body region and a second sensor at a second body region that is a contralateral region to the first body region. In one variation, as shown in FIG. 3B, for a garment 105 that has a form factor of a top (e.g., shirt, tank top, etc.), the set of biometric sensors 120 can include a set of EMG electrodes configured to be positioned at desired locations when the garment 105 is worn by the user, and can additionally or alternatively include one or more of a heart rate sensor and a respiratory sensor. In one example of this variation, the set of EMG electrodes include electrodes configured to be positioned proximal one or more of: the pectoralisis muscles, the abdominal muscles, the oblique muscles, the trapezius muscles, the rhomboid muscles, the teres major muscles, the latissimus dorsi muscles, the deltoid muscles, the biceps muscles, and the triceps muscles when the garment 105 is worn by the user. In the example, the set of biometric sensors can further include a heart rate sensor configured to be positioned proximal the heart region of the user, and/or a respiratory sensor configured to encircle at least a portion of the torso of the user (i.e., to facilitate plethysmography) when the garment 105 is worn by the user. Variations of the example of the garment 105 configured as a top with biometric sensors can, however, be configured in any other suitable manner (e.g., a tank top garment can omit sensors positioned proximal the triceps and the biceps muscles).

Figure 3C:
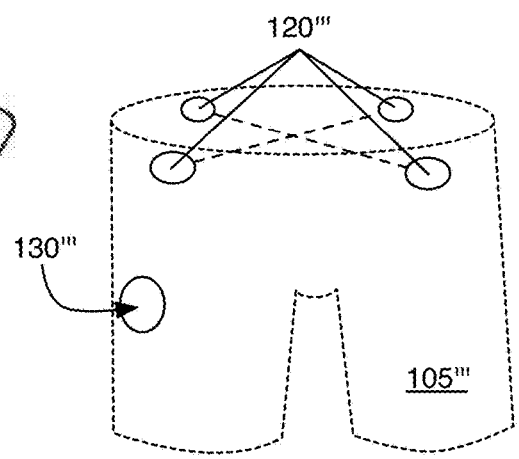
Figure 3D:
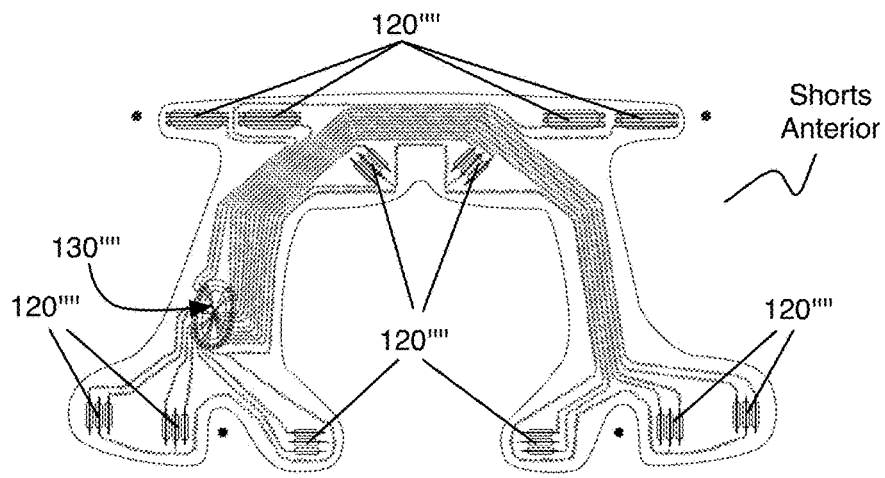
FIG. 3D depicts a specific example of a biometric sensor configuration in an embodiment of a system for monitoring biometric signals of a user.

In another variation, as shown in FIGS. 3C and 3D, for a garment 105 that has a form factor of a bottom (e.g., shorts, pants, etc.), the set of biometric sensors 120 can include a set of EMG electrodes configured to be positioned at desired locations when the garment 105 is worn by the user. In one example of this variation, the set of EMG electrodes include electrodes configured to be positioned proximal one or more of: the gluteus maximus muscles, the gluteus medius muscles, the vastus lateralis muscles, the gracilis muscles, the semimembranosus muscles, the semitendinosis muscles, the biceps femoris, the quadriceps muscles, the soleus muscles, the gastrocnemius muscles, the rectus femoris muscles, the sartorius muscles, the peroneus longus muscles, and the adductor longus muscles when the garment 105 is worn by the user. Variations of the example of the garment 105 configured as a bottom with biometric sensors can, however, be configured in any other suitable manner.

In alternative embodiments, the set of biometric sensors 120 can be supplemented with a set of supplementary sensors 125 configured to detect one or more aspects associated with an environment of the user. In variations, the set of supplementary sensors 125 can include one or more of: environmental temperature sensors, altimeters, oxygen content sensors, air quality sensors, near field communication (NFC) sensors (e.g., configured to detect a nearby device or piece of exercise equipment having a corresponding NFC element), and any other suitable supplementary sensor that can enrich the data acquired from user and/or the environment of the user.

The control module 130 comprises a housing 140 and a set of contacts 150 configured to couple to an array of connection regions 115 in electrical communication with the set of biometric sensors 120, which enable signal transmission from the set of biometric sensors to the control module 130. The control module 130 preferably also includes an electronics subsystem 160 in communication with the set of contacts 150, wherein the electronics subsystem 160 facilitates signal reception, signal conditioning, signal transmission, and power distribution for the system 100. The control module 130 thus functions to control signal reception, preprocessing, and transmission to a processing subsystem, and to physically protect/isolate sensitive elements (e.g., electronics) of the system 100. The control module 130 is preferably configured to be a portable control module that can removably couple to the garment 105 and set of biometric sensors 120 in cooperation with a mounting module no of the garment 105, as described below. As such, the control module 130 can be configured to be uncoupled from the garment by the user (or another entity) when desired (e.g., during charging, during washing of the garment, during battery replacement, etc.). However, the control module 130 can alternatively be configured to semipermanently couple to the garment 105, such that it is not desirable for the user to remove the control module 130 from the garment.

The housing 140 functions to house and protect the electronics subsystem 160 over the lifetime of use of the system 100 by a user, and can further function to enhance wearability of the system. The housing 140 is preferably composed of a rigid material (e.g., a rigid plastic material, a metal, etc.), such that the housing 140 does not deform in response to normal forces, shear stresses, bending stresses, or torsional stresses induced during use of the system 100. Alternatively, the housing 140 can be flexible to facilitate maintenance of compliance with a user as the user performs a physical activity. In variations wherein the housing 170 is flexible, other elements of the system 100 can also be flexible (e.g., the electronics subsystem can comprise a flexible thin film battery, the electronics subsystem can comprise flexible electronics, etc.) to facilitate compliance with the body of a user. In a specific example, the housing is composed of a polycarbonate/acyrlonitrile butadiene styrene (ABS) blend; however, variations of the specific example can alternatively be composed of only polycarbonate, only ABS, or any other suitable material.

Figure 4A:
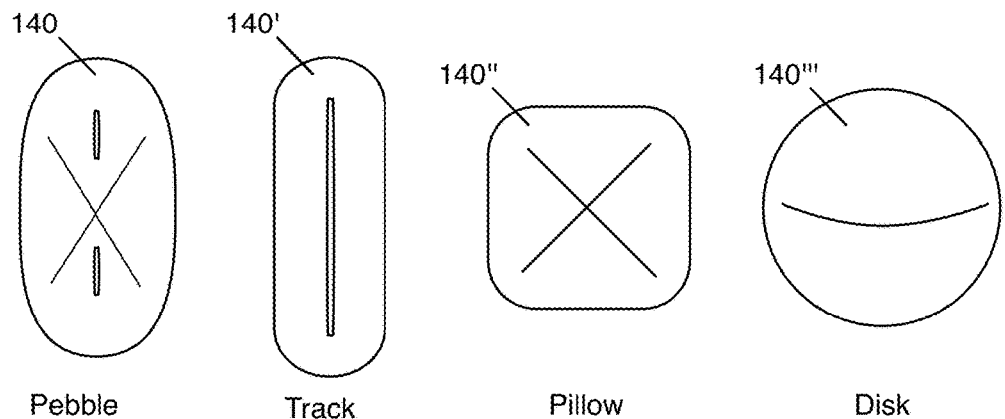
FIG. 4A depicts variations of a housing of a control module in an embodiment of a system for monitoring biometric signals of a user.
Figure 4B:
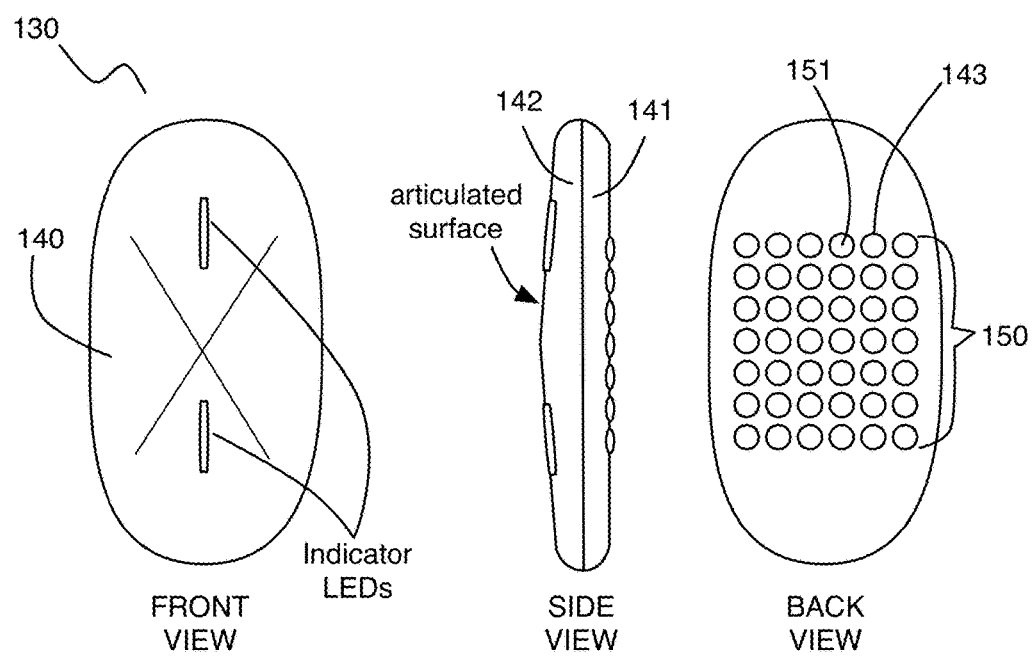
FIG. 4B depicts an example of a control module in an embodiment of a system for monitoring biometric signals of a user.

The housing 140 preferably has a profile that does not protrude a significant distance from the body of the user when the garment 105 is worn by the user. As such, the housing 140 preferably has a low aspect ratio that contributes to a thin form factor of the control module 130. However, the housing 140 can alternatively define a volume with a high aspect ratio. Preferably, the external surface of the housing 140 is substantially smooth and has rounded edges, in order to avoid damaging the garment 105 during motion of the user. Furthermore, the housing 140 can define a substantially polygonal footprint (i.e., triangular footprint with rounded edges, a quadrilateral footprint with rounded edges, a pentagonal footprint with rounded edges, a hexagonal footprint with rounded edges, etc.), or can alternatively define one or more of a circular footprint, an ellipsoidal footprint, and an amorphous footprint. In one example, as shown in FIG. 4B, the housing 140 defines an ellipsoidal footprint and has a thickness substantially below 2 cm, a height below 10 cm, and a width below 6 cm, in order to produce a smooth form factor with a low aspect ratio. In a specific example, as shown in FIG. 4B, the housing 140' has an ellipsoidal footprint with an overall thickness of 11 mm, a shell thickness of 1.4 mm, a width of 34 mm, and a height of 62 mm. Variations of the example of the housing can, however, be configured in any other suitable manner, as shown in FIG. 4A.

The housing 140 preferably forms a shell about internal components of the control module 130, and preferably has a first housing surface 141 facing the body of the user when the control module 130 interfaces with the user and a second housing surface 142 facing away from the body of the user when the control module 130 interfaces with the user, an example of which is shown in FIG. 4B. The first housing surface 141 and/or the second housing surface 142 can comprise a concave surface or a convex surface, in interfacing with the garment or the body of the user. Furthermore, depending upon the intended position of the control module 130 relative to the garment 105 and/or the body of the user, the first housing surface 141 and/or the second housing surface 142 can define surfaces that are configured to conform to the body of the user upon coupling of the system 100 to the user. The first housing surface 141 and the second housing surface 142 can be coupled together using a hermetic sealing element, including one or more of: an adhesive, a compliant sealing material (e.g., putty), an o-ring, an x-ring, any other suitable ring, and/or any other suitable sealing element. As such, an interface between the first housing surface 141 and the second housing surface 142 can be configured to be waterproof and/or machine-washable in order to protect aspects of the control module 130. In the specific example shown in FIG. 4B, the first housing surface 141 has an articulated surface configured to promote tactility, and ports that allow light transmission (e.g., from indicator LEDs) to inform the user regarding one or more statuses of the system 100 (e.g., proper coupling relative to other elements of the system 100, an active configuration of the control module 130, an inactive configuration of the control module 130, a charging status of the system 100, a calibration status of the system 100, etc.).

The housing 140 preferably has an array of openings 143 defined at one or more of the first housing surface 141 and the second housing surface 142, wherein the array of openings 143 provides access for a set of contacts 150 configured between the electronics subsystem 160 and an array of connection regions 115, as described in further detail below. Preferably, the array of openings 143 is defined entirely at the first housing surface 141; however, in alternative variations, the array of openings 143 can be defined at both the first housing surface 141 and the second housing surface 142, or at only the second housing surface 142. The array of openings 143 can comprise a rectangular array of openings; however, the array of openings 143 can alternatively be configured in any other suitable manner (e.g., as a circular array of openings, as an ellipsoidal array of openings, as a polygonal array of openings, as an amorphous array of openings, etc.). Each opening in the array of openings 143 can be a circular opening or can alternatively be a non-circular opening. Furthermore, each opening in the array of openings 143 is preferably identical to every other opening in the array of openings 143 in morphology; however, the array of openings 143 can alternatively comprise non-identical openings. In a specific example, as shown in FIG. 4B the array of openings 143 includes 42 identical circular openings arranged in a 7×6 rectangular array, each opening having a diameter of 3 mm and an inter-opening spacing of 1.5 mm; however, variations of the specific example of the array of openings 143 can be configured in any other suitable manner.

The set of contacts 150 functions to facilitate coupling between the electronics subsystem 160 of the control module 130 and an array of connection regions 115, by way of the array of openings 143 of the housing 140 described above. As such, the set of contacts 150 comprise electrically conductive contacts that facilitate reception of biosignals from the set of biometric sensors 120 of the system 100. Preferably, the set of contacts 150 comprises contacts composed of an electrically conductive, elastic, and compliant material (e.g., electrically conductive silicone, electrically conductive polymer, etc.) that facilitates maintenance of electrical communication between the set of biometric sensors 120 and the electronics subsystem 160 during motion of the user. In one example, the conductive polymer used in the set of contacts comprises an ether-based conductive thermoplastic polyurethane material; However, the set of contacts 150 can alternatively comprise one or more contacts composed of an electrically conductive, but non-elastic or non-compliant material (e.g., a metallic material).

Figure 5A:
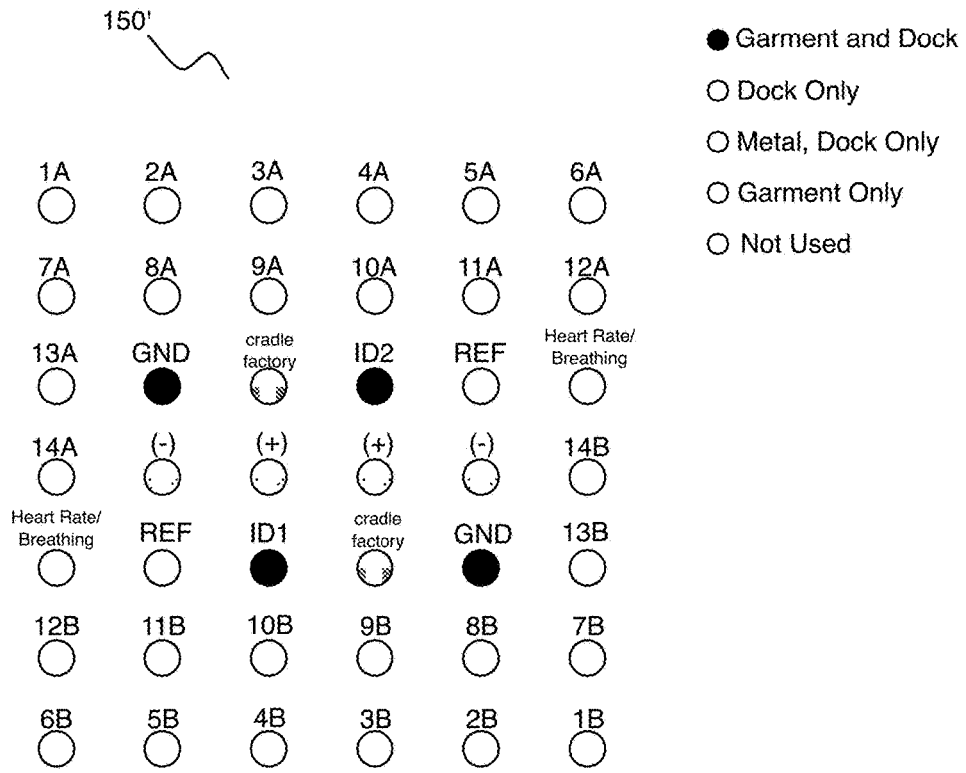
FIG. 5A depicts a first example configuration of contacts in an embodiment of a system for monitoring biometric signals of a user.
Figure 5B:
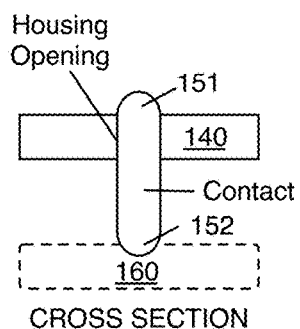
FIG. 5B depicts a cross-section of a portion of an embodiment of a system for monitoring biometric signals of a user.

As shown in FIG. 5B, each contact in the set of contacts 150 preferably includes a first region 151 that extends through at least one opening of the array of openings 143 of the housing 140, and a second region 152 that couples to a portion of the electronics subsystem 160 configured for signal reception/conditioning. The first region 151 of each contact in the set of contacts 150 preferably hermetically seals at least one opening in the array of openings 143 of the housing 140, in order to prevent fluids (e.g., water, sweat) from seeping into the housing and potentially damaging the electronics subsystem 160, which is otherwise accessible through the array of openings 143. As such, the housing 140 of the control module 130 is preferably configured to be waterproof and/or machine-washable, due to the configuration of the set of contacts 150 in relation to the housing 140. The first region 151 of each of the set of contacts 150 can thus be over-molded on the housing 140 at least at one opening of the array of openings 143, and the second region 152 can be over-molded onto or otherwise coupled to a desired region of the electronics subsystem 160, which is internal to the housing 140 of the control module 130. Each contact in the set of contacts 150 is preferably associated with an opening of the array of openings 150 in a one-to-one manner; however, the set of contacts 150 and the array of openings 143 can alternatively be configured in a less-than-one-to-one or a more-than-one-to-one manner.

In relation to the configuration of the set of contacts 150, the contacts can each be assigned to and facilitate signal reception from a corresponding biometric sensor of the set of biometric sensors 120. Additionally, in some configurations, each contact and biometric sensor can be associated with a companion contact and biometric sensor to facilitate detection of a signal differential (i.e., a biopotential difference) across two paired biometric sensors. As such, the control module 130 can utilize signals from paired sensors in measuring a biopotential difference, thereby enabling determination of one or more metrics associated with muscle/exercise activity. In a first variation, the set of contacts 150 can be arranged according to pins on corresponding circuitry of the electronics subsystem 160. In the first variation, as shown in FIG. 5A, the set of contacts 150' can be arranged in a symmetrically opposing arrangement about any suitable axis of symmetry (e.g., a diagonal axis of symmetry defined by the array of openings 143 of the housing, a horizontal axis of symmetry defined by the array of openings 143 of the housing, a vertical axis of symmetry defined by the array of openings 143 of the housing, etc.). In an example of the first variation, contact 1A, as shown in the top left corner of the set of contacts shown in FIG. 5A, can be paired with contact 1B in the bottom right corner of the set of contacts 150, in facilitating detection of a first biopotential difference determined from two paired biometric sensors. In the example, the set of contacts 150 further comprises contacts associated with paired heart rate/respiratory signal detection sensors, ground pins of the electronics subsystem 160, and identification pins of the electronics subsystem 160.

Figure 6:
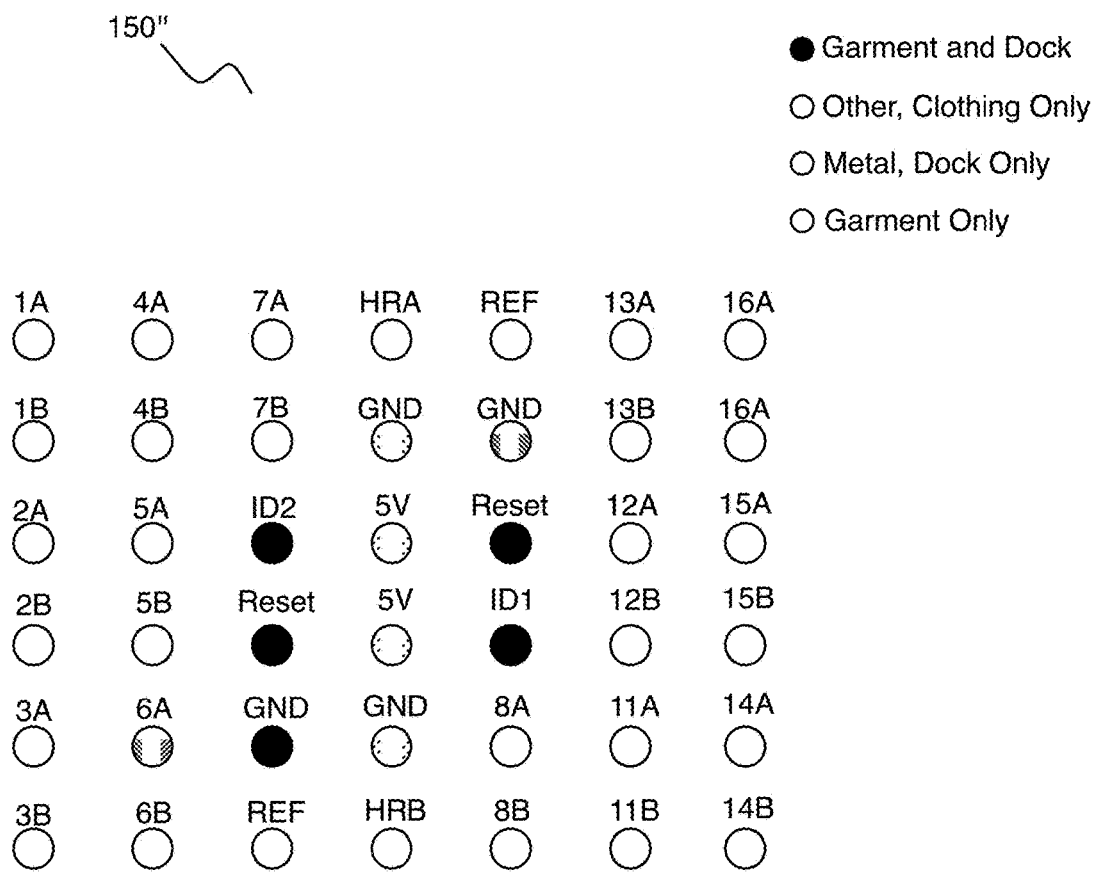
FIG. 6 depicts a second example configuration of contacts in an embodiment of a system for monitoring biometric signals of a user.

In a second variation, as shown in FIG. 6, the set of contacts 150" can be arranged such that associated pairs of contacts are positioned proximal to each other. In an example of the second variation, contact 1A, as shown in the top left corner of the set of contacts shown in FIG. 6, can be paired with contact 1B just below contact 1A (in the orientation shown in FIG. 6), in facilitating detection of a first biopotential difference determined from two paired biometric sensors. In the example, the set of contacts 150 further comprises contacts associated with paired heart rate/respiratory signal detection sensors, ground pins of the electronics subsystem 160, and identification pins of the electronics subsystem 160.

Variations of the first and the second variations of contact configurations can comprise any other suitable combination of symmetrically opposing arrangements of paired contacts and proximal placement of paired contacts. For instance, a portion of paired contacts associated with biometric sensors can be proximally placed, while other contacts (e.g., contacts associated with identification pins, contacts associated with ground pins, etc.) can be arranged in a symmetrically opposing arrangement.

In any of the above contact configurations, and for control modules 130 with housings 140 that can be coupled with the garment 105 in multiple orientations (e.g., for a control module 130 that has a housing 140 with at least one axis of symmetry), the control module can be configured to utilize the contact configuration(s) and any other suitable data (e.g., accelerometer data, gyroscope data) in order to detect the orientation of the control module relative to the garment 105, and to adapt signal reception and processing functions accordingly. As such, the control module 130 can be configured to operate properly regardless of how the control module is coupled with the garment 105. Thus, a user would not need to ensure that the control module 130 is coupled with the garment 105 according to a specific orientation (e.g., based upon alignment marks on the control module, based upon asymmetry of the control module, etc.). Additionally, the control module 130 and contact configurations can have associated firmware to facilitate correct mapping between the set of contacts 150 and the set of biometric sensors 120 in a desired manner. For example, using the contact configuration shown in FIG. 6, signals X and Y can be received by way of contacts 1A and 1B in a first orientation of the control module 130, but if the control module is positioned "upside-down" in a second orientation, firmware can adapt signal reception and processing of the control module to receive signals X and Y by way of contacts 14B and 14A, respectively. As such, in the example, the control module 130 can be configured to dynamically modify the contact mapping in order to property attribute signals X and Y to the correct muscle group or set of biometric sensors. Alternatively, the control module 130 and/or housing 140 can be configured to couple with the garment 105 in only a single orientation (e.g., based upon markings, based upon asymmetry in the control module 130 or housing, etc.), such that the control module 130 does not require firmware that enables adaptive coupling.

The electronics subsystem 160 is configured to be in electrical communication with the set of contacts 150, and functions to facilitate signal reception, signal conditioning, signal transmission, and power distribution for the system 100. The electronics subsystem 160 is preferably housed within an internal portion of the housing 140 of the control module 130, in order to be isolated from mechanisms that could damage the electronics subsystem 160; however, the electronics subsystem 160 can alternatively be configured in any other suitable manner. The electronics subsystem 160 preferably comprises a power module 161, a supplementary sensing module 163, a signal conditioning module 165, a communication interface 167, and memory 169; however, the electronics subsystem 160 can additionally or alternatively include any other suitable element(s) that enrich acquired data and/or facilitate conditioning or processing of signals from the user as the user performs a physical activity.

The power module 161 of the electronics subsystem 160 functions to provide regulated and unregulated electrical power to the system 100 and to allow power storage for the system 100. The power module 161 preferably comprises a rechargeable battery 162 (e.g., a lithium-ion battery, nickel-cadmium battery, metal halide battery, nickel metal hydride battery, lithium-ion polymer battery, etc.); however, the power module 161 can alternatively comprise a non-rechargeable battery (e.g., alkaline battery) that can be replaced to further enhance modularity in the system 100. Preferably, the power module 161 is configured to have a profile with a low aspect ratio, contributing to a thin form factor of the control module 130/housing 140. However, the power module 161 can be configured to have any other suitable profile such that the power module 161 provides adequate power characteristics (e.g., cycle life, charging time, discharge time, etc.) for the system 100.

In variations where the battery 162 of the power module 161 is rechargeable, the electronics subsystem 160 can also comprise a coil of wire and associated electronics that function to allow inductive coupling of power between an external charging element 62 and the power module 161, as shown in FIGS. 1 and 9A-9B. The charging coil preferably converts energy from an alternating electromagnetic field (e.g., provided by a charging dock or other adapter), into electrical energy to charge the battery 162 and/or to power the system 100. Inductive charging allows electrical isolation between the external charging element 62 and internal electronics of the electronics subsystem 160 to promote user safety and convenience in interfacing with the system 100. Inductive charging provided by the charging coil thus also facilitates user mobility while the user interacts with the system 100, such that the user can perform a wide range of physical activities while having his/her biometric signals monitored by the system 100. In alternative variations, however, the charging coil can be altogether omitted (e.g., in variations without a rechargeable battery), or replaced or supplemented by a connection (e.g., USB connection) configured to provide wired charging of a rechargeable battery.

The supplementary sensing module 163 functions to facilitate acquisition of additional data from the user, which can be used to trigger control of aspects of signal acquisition and/or analysis generation by the control module 130. As such, not all sensors of the system 100 may be separate from the control module 130. The supplementary sensing module 163 preferably includes a set of supplementary sensors 164 configured to detect one or more aspects associated with motion of the user and/or an environment of the user. In variations, the set of supplementary sensors 125 can include one or more of: an accelerometer (e.g., a single axis accelerometer, a multi-axis accelerometer), a gyroscope (e.g., a single axis gyroscope, a multi-axis gyroscope), a GPS module, environmental temperature sensors, altimeters, oxygen content sensors, air quality sensors, near field communication (NFC) sensors (e.g., configured to detect a nearby device or piece of exercise equipment having a corresponding NFC element), and any other suitable supplementary sensor that can enrich the data acquired from user and/or the environment of the user. In one example, accelerometers of the supplementary sensing module 163 can be used to detect a type of physical activity (e.g., cardio exercise, weight training exercise, etc.) performed by the user, and/or can be used during signal processing to remove motion-produced artifacts from signals being processed. The supplementary sensing module 163 can, however, comprise any other suitable sensors and be configured relative to the electronics subsystem 160 in any other suitable manner.

The signal conditioning module 165 functions to preprocess signals detected and received using the set of biometric sensors and/or sensors of the supplementary sensing module 163, thereby producing conditioned data prior to processing. In variations, the signal conditioning module 165 can comprise elements configured to perform any one or more of: filtering (e.g., using a low pass filter, a high pass filter, a band-pass filter, a notch filter, etc.), smoothing, clipping, deconvolving, detrending/offsetting, standardizing, resampling, hard-binding, predicting, windowing, and any other suitable data conditioning process upon any signals received from the set of biometric sensors 120. The signal conditioning module can thus comprise one or more of: filters, amplifiers, analog-to-digital converters (ADCs), digital-to-analog converters (DACs), signal multiplexers, and any other suitable elements for conditioning signals received from biometric sensors and supplementary sensors.

The communication interface 167 preferably comprises hardware and/or software elements configured to facilitate communication of information between the set of biometric sensors 120 and the control module 130, and/or communication of information between the control module 130 and one or more separate devices (e.g., a processing subsystem, a mobile computing device of the user, etc.). As such, the communication interface 167 can function as a data link that provides a means for communications to and from the control module 130 over a network. The network can comprise any suitable network used for communication between electronic devices. The network can include a wireless and/or a wired connection between devices. In examples of wireless connections, the network associated with the communication interface 167 can include any one or more of: a local area network (LAN), a wireless LAN (WLAN), a Bluetooth network (e.g., a Bluetooth Low Energy network), a municipal area network (MAN), a wide area network (WAN), the internet, and any other suitable network. Furthermore, in some variations, the communication interface 167 can include features that provide security in information communication. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In wired variations of the communication interface 167, the communication interface can implement any one or more of an audio jack connection (e.g., AUX cable), a USB connection, a parallel port, a serial port, an ethernet adapter, an IEEE 1394 bus interface, a small computer system interface (SCSI) bus interface, an infrared (IR) communication port, and any other suitable wired or hardware connection. In this variation, the communication interface 167 can communicate with other devices over a network using one or more of: inter-integrated circuit communication (I2C), one-wire, master-slave, or any other suitable communication protocol. However, the communication interface 167 can transmit data in any other way and can include any other type of wired connection that supports data transfer between the electronics subsystem 160, external devices, and/or any other suitable computing element.

The memory 169 functions to retain data from signals received at the electronics subsystem 160. As such, upon receiving signals from the set of biometric sensors 120, the electronics subsystem 160 of the control module 130 can thus facilitate storage of biometric data (e.g., conditioned data from biopotential signals, unconditioned data from biopotential signals) within memory of the electronics subsystem 160. The memory 169 can comprise processor-readable medium including any one or more of: random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and any other suitable storage element. Preferably, data from the memory 169 is automatically transmitted to any appropriate external device, over a network, substantially continuously (e.g., every second, every millisecond, etc.); however, data from the data storage unit 180 can alternatively be transmitted intermittently (e.g., every minute, hourly, daily, or weekly). In one example, data generated by any element of the system 100 may be stored in memory 169 when the communication interface 167 is not actively coupled to an element external to the electronics subsystem 160 over the network. However, in the example, when a link is established between the communication interface 167 and an external element, data may then be automatically transmitted from memory 169. In other examples, the memory 169 can additionally or alternatively be manually prompted to transmit stored data, when prompted by a user or other entity.

Figure 12:
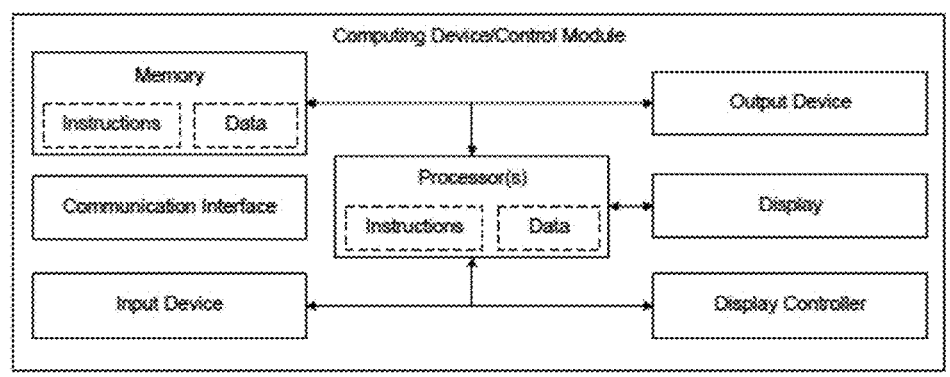
FIG. 12 depicts an embodiment of a portion of a system for monitoring biometric signals of a user.

The control module 130 can, however, include any other suitable elements, including input devices (e.g., keyboard, mouse, microphone, remote control, button, joystick, trackball, touchpad, optical sensor), wherein the input device(s) can receive input from another device, and output devices (e.g., displays, projectors, speakers, tacticle devices, network cards, wireless transmitters, infrared transmitters, lights, etc.) that convey information to a user, as shown in FIG. 12. For instance, an output device associated with the control module 130 can display a graphical user interface (GUI) that facilitates user interaction. Such a display can utilize any suitable image projection technology, such as a cathode ray tube (CRT), liquid crystal display (LCD), light-emitting diode (LED), gas plasma, electroluminescence, or any other suitable image projection technology.

Figure 7A:
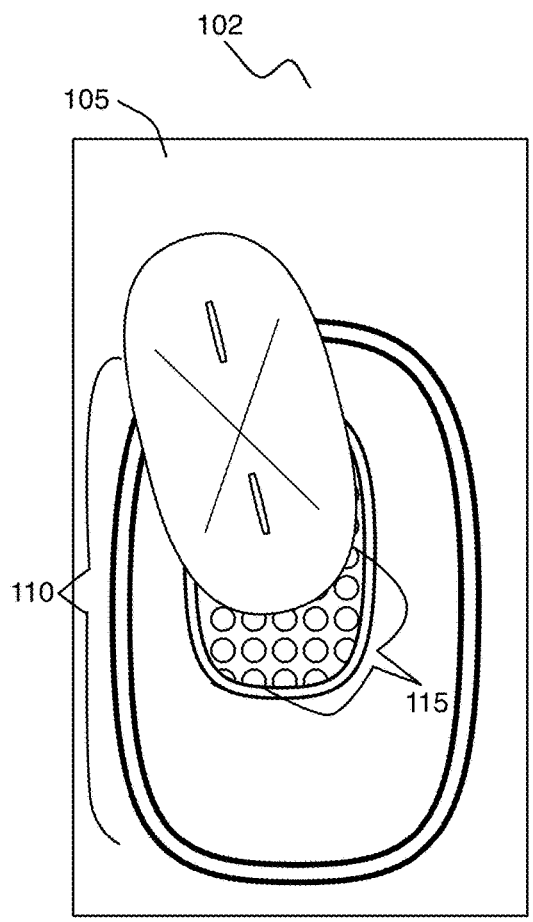
FIGS. 7A-7B depict a first configurations and a second configuration, respectively, of coupling between a control module and an array of connection regions in an embodiment of a system for monitoring biometric signals of a user.
Figure 7B:
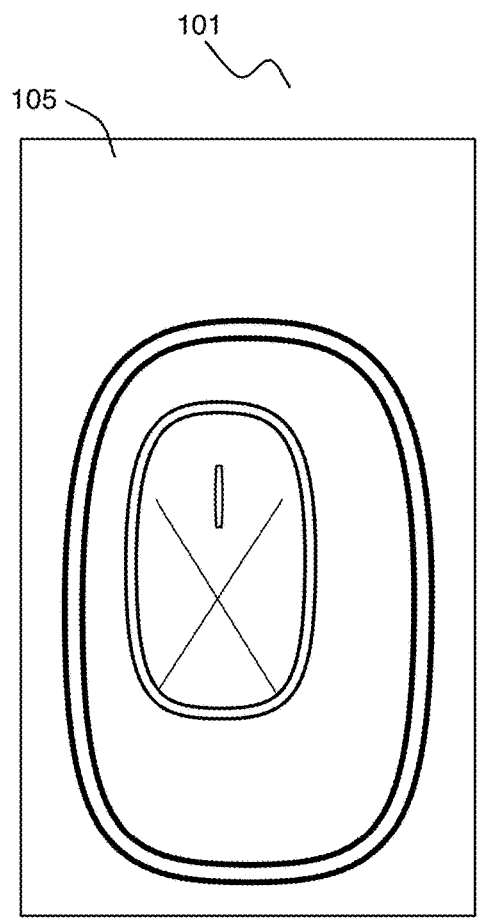

In relation to coupling between the control module 130 and the garment 105, the system 100 can also include a mounting module no, as shown in FIGS. 7A and 7B, that receives the control module 130 in order to facilitate coupling of the control module 130 to the garment 105 in a reversible and repeatable manner. The mounting module 110 thus preferably provides an array of connection regions 115, which function to facilitate electrical coupling between the set of biometric sensors 120 and the set of contacts 150 of the control module 130 in a first configuration 101. As such, the garment 105 can also function to serve as a substrate for facilitating electrical coupling between the set of biometric sensors and the mounting module 115. In variations, the mounting module no and/or the garment 105 can include any one or more of: slots, pouches, ports, bases, pathways, channels, cradles, and any other suitable feature by which the set of biometric sensors and/or control module 130 can be permanently or removably coupled to each other and/or to the mounting module 110 or the garment 105. Furthermore, the garment 105 can include conductive leads (e.g., wires, conductive filaments) passing along and/or throughout the garment 106 to enable signal transmission between the mounting module no and the set of biometric sensors 120 (e.g., by way of the plurality of conductive regions 106 of the garment 105). Alternatively, the garment 105 or any other element of the system 100 can be configured to facilitate wireless communication between the set of biometric sensors 120 and the control module 130. In one such example, the garment 105 and other elements of the system 100 can be configured according to an embodiment, variation, or example described in U.S. Application No. 62/077,781, entitled "Biometric Monitoring Garment" and filed on 10 Nov. 2014.

The mounting module 110 thus functions to provide an electrical and mechanical interface between the control module 130 and the set of biometric sensors 120 of the garment 105, in facilitating signal transmission in a robust manner as the user performs a physical activity. In producing a robust electrical and mechanical interface, the mounting module no can comprise a set of layers 111 coupled to each other and/or to a surface of the garment 105, wherein the set of layers provide a biasing force that maintains contact between the set of contacts 150 of the control module and the array of connection regions 115 of the mounting module no. In generating the biasing force, the set of layers 111 can include one or more of elastic layers (e.g., elastic fabrics), compliant layers (e.g., foam layers), and substantially rigid layers (e.g., layers that are configured to accommodate the control module 130 in a press-fit or snap-fit manner). As such, the mounting module 110 provides a robust electromechanical connection between the control module 130 and the array of connection regions 115 of the mounting module 110 in a first configuration 101, and enables decoupling of the control module 130 from the mounting module 110 in a second configuration.

Figure 8A:
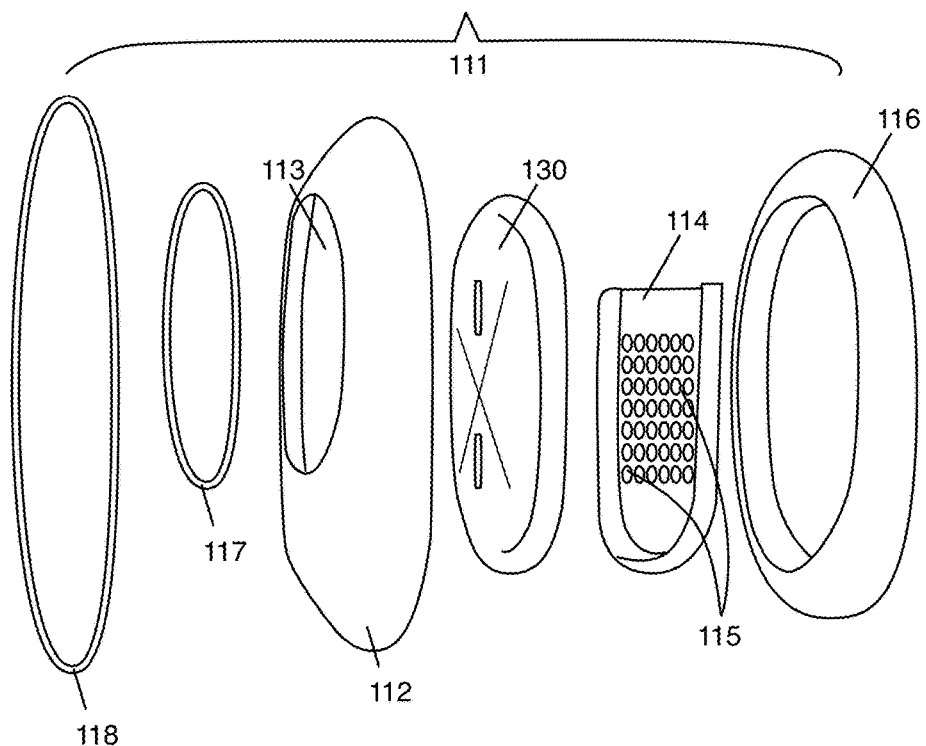
FIG. 8A depicts an example of a mounting module in an embodiment of a system for monitoring biometric signals of a user.

In one example, as shown in FIG. 8A, the mounting module no comprises: a fabric layer 112 affixed to the garment 105 and defining a receiving pocket for the control module 130, wherein the fabric layer 112 has an elastic opening 113 that accommodates reception of the control module 130 and exposes one or more indicator LEDs of the control module 130; a cradle 114 deeper than the fabric layer 112 and comprising the array of connection regions 115 that couple to the set of biometric sensors 120; a foam ring 116 at least partially surrounding the cradle 114 and deeper than the fabric layer 112, wherein the foam ring 116 functions to provide stability to a control module 130 seated within the fabric layer 112 at the cradle 114, and can further function to protect the user from the rigidity of the cradle as well as shielding regions where sensor leads are coupled to the cradle 114; a first tape ring 117 surrounding at least a portion of the elastic opening 113 of the fabric layer 112; and a second tape ring 118 surround at least a portion of the periphery of the fabric layer 112, wherein the first tape ring 117 and the second tape ring 118 function to provide structural integrity to the fabric. The mounting module no can, however, comprise a configuration such as that described in U.S. Provisional Application Ser. No. 62/013,405 filed 17 Jun. 2014, and/or U.S. Provisional Application Ser. No. 62/016,373 filed 24 Jun. 2014, both entitled "Biometric Monitoring System". Additionally or alternatively, variations of the mounting module 110 can comprise combinations of any of the above variations and examples, or any other suitable configuration of a mounting module.

Figure 8B:
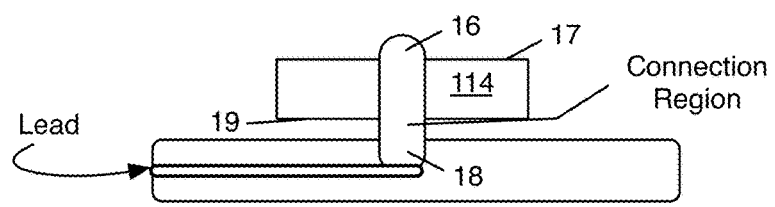
FIG. 8B depicts a cross section of a portion of an embodiment of a system for monitoring biometric signals of a user.

In the example, and with regard to the cradle 114, the cradle 114 is preferably composed of a rigid material (e.g., rigid plastic) having the array of connection regions 115 arranged in a configuration that is complementary to the set of contacts 150 of the control module no. As such, in the example, the array of connection regions 115 comprises a 7×6 array of circular connection regions configured to couple with the 7×6 array of circular contacts of the control module 130. In the example, each connection region of the array of connection regions 115 comprises a conductive silicone rubber; however, the connection regions can additionally or alternatively be composed of any other suitable material. Similar to the set of contacts 150, and as shown in FIG. 8B, each connection region in the array of connection regions can have a first region 16, exposed through a first cradle surface 17 configured to contact the first region 151 of at least one contact, and a second region 18 in communication with the first region 16 and configured to couple to a lead proximal a second cradle surface 19, wherein the lead enables electrical communication between a connection region of the array of connection regions 115 and at least one biometric sensor of the set of biometric sensors 120. As such, each connection region of the array of connection regions 115 of the mounting module no can be in communication (e.g., by way of one or more leads) to one or more corresponding biometric sensors 120, as described above.

Thus, the set of layers in of the example function bias the set of contacts 150 of the control module 130 into electromechanical communication with the array of connection regions 115 of the mounting module 110, to enable reception of biopotential signals from the set of biometric sensors 120 at the control module 130.

The location of mounting module no is preferably dependent upon the type(s) of garment(s) included in the system 100. For instance, for a garment 105 configured as a top, the mounting module 110 is preferably located at a position that does not interfere with physical activity (e.g., weight lifting activity) of the user, generate significant signal interference with one or more of the set of biometric sensors 120, or interfere with the user/signal reception in any other suitable manner. In one example, the mounting module no can be positioned proximal the triceps or biceps muscle of the user, when the garment 105 is worn by the user. In another example, the mounting module 110 can be centrally located between the pectoralis muscles of the user and/or the abdominal muscles of the user, when the garment 105 is worn by the user. In another variation wherein the garment 105 is configured as a bottom, the mounting module 110 can be located proximal the vastus lateralis muscle(s) of the user when the garment 105 is worn by the user. Additionally or alternatively, the system 100 can comprise multiple mounting modules no, such that the control module can be repositioned when the user is performing different types of physical activity. For example, a first mounting module positioned at an anterior portion of the garment 105 can allow the user to comfortably perform sit-ups or other exercises where the user is lying face-up, and a second mounting module positioned at a posterior portion of the garment 105 can allow the user to comfortably perform exercise where the user is lying face-down.

As noted earlier with respect to embodiments of the control module 130 including indicator LEDs, the mounting module no preferably allows light from the indicator LEDs to be visualized by the user wearing the garment 105. In one variation, upon insertion of the control module 130 into the mounting module no, exposed LED indicators can be activated (e.g., by the control module 130) in order to indicate that the control module 130 has been properly seated within the mounting module 110 and is in a state to receive signals from the set of biometric sensors 120. As such, in coupling with the mounting module no, the control module 130 can perform one or more of: detecting proper seating within the mounting module 110, determining an orientation of the control module 130 within the mounting module no, determining, based upon the orientation of the control module, which indicator LED(s) are exposed to the user, activating the exposed indicator LED(s), not activating the unexposed indicator LED(s), and performing any other suitable function.

While the array of connection regions 115 is described in relation to the mounting module 110, the array of connection regions 115 can alternatively be integrated with the garment 105, in variations of the system 100 wherein the control module 130 is not configured to be removably coupleable to the garment 105 by way of a mounting module no. As such, variations of the system 100 can alternatively omit a mounting module 110 and instead provide direct coupling between the set of biometric sensors 120 and the control module 130 without an intermediate mounting module no. Variations of the system 100 can, however, be configured in any other suitable manner.

Additionally or alternatively, the mounting module 110 can comprise a first locking portion that is configured to interact with a second locking portion on the housing 140 of the control module 130, in order to facilitate maintenance of contact between the set of contacts 150 of the control module 130 and the array of connection regions 115 of the mounting module no. In one example, the housing 140 of the control module 130 can define a notch 401 configured to reversibly couple with a latch 402 of a portion of the mounting module 110, as shown in FIG. 8C. However, the housing 140 of the control module 130 can be configured to reversibly or irreversibly lock with the mounting module no using any other suitable mechanism, including one or more of a snap fit mechanism, a press fit mechanism, a magnetic mechanism, and any other suitable mechanism.

In some variations, the system 100 can further include a processing subsystem 170 configured to communicate with the electronics subsystem 160 and generate analyses based upon biometric signals detected by way of the set of biometric sensors. The processing subsystem 170 is preferably configured to perform at least a portion of the method 200 described in section 2 below; however, the processing subsystem 170 can alternatively be configured to perform any other suitable method. As such, the processing subsystem 170 is configured to be in communication with the electronics subsystem 160 over the network associated with the communication interface, and can further be configured to be in communication with an electronic device 180 of the user over the network. As such, analyses generated using the processing subsystem 170 can be transmitted to the electronic device 180 of the user in order to inform the user regarding his/her exercise behavior.

The processing subsystem 170 can comprise any suitable general purpose processing subsystem, which can include any one or more of: a central processing unit (CPU), a microprocessor, a digital signal processor (DSP), a microcontroller, a cloud-based computing system, a remote server, a state machine, an application-specific integrated circuit (ASIC), a programmable logic device (PLD), a field programmable gate array (FPGA), any other suitable processing device, and any suitable combination of processing devices (e.g., a combination of a DSP and a microprocessor, a combination of multiple microprocessors, etc.). For instance, in some variations, the processing subsystem 170 can be implemented in multiple modules including one or more of a DSP module of the electronics subsystem 160 having embedded algorithms, a module executing on a remote server, a module executing in a cloud-based computing system, and any other suitable module.

One or more of the elements of the electronics subsystem 160 and the processing subsystem 170 can be implemented in coordination with an electronic device 180 of the user or in proximity to the user, as the user performs physical activities. For instance, a mobile device and/or a wearable computing device (e.g., head-mounted computing device, wrist-mounted computing device, etc.) can implement indication, processing, and/or analysis provisions of the system 100, in cooperation with other elements of the system 100.

Additionally or alternatively, the electronic device 180 of the user can facilitate execution of an exercise monitoring application, in cooperation with data processing, analysis generation, and information transmission from other elements of the system 100. The exercise monitoring application can implement hardware and/or software components used for obtaining activity data from the system 100, and for performing operations on and analyses of the activity data. In one variation, the exercise monitoring application can utilize the activity data to determine one or more exercise-related metrics (e.g., total effort output, average heart rate throughout a workout, average heart rate throughout a portion of a workout, a breakdown of muscle exertion for different muscle groups, exercise progress-related metrics, etc.) representative of the user's exercise behavior, and can additionally or alternatively generate a report including the exercise-related metrics and present the report to the user within a graphical user interface (e.g., incorporating a display device, incorporating a touchscreen device). Thus, the exercise monitoring application can allow the user to monitor effectiveness of one or more exercise activities he/she performs, as well as progress in aspects of the user's performance of one or more exercise activities. In utilizing the GUI provided by the electronic device 180, the electronic device 180 can be configured to display a virtual representation of different muscle groups of the user, and/or a graphic that depicts near-real-time feedback of muscle activity of the user in association with the virtual representation of different muscle groups of the user. As such, exercise-monitoring application executing on the electronic device 180 can be used to provide near-real-time feedback to the user as the user is performing a workout regimen.

Similar to other elements of the system 100, the electronic device 180 can include a storage module configured to store activity data, performance data, and/or generated reports within a database. The storage module can be implemented at the electronic device 180 and/or on a remote computing device, and preferably facilitates documentation and provision of historical exercise information to the user. Similar to the control module 130, the electronic device 180 can further include a communication interface that allows the electronic device to communicate information over the network associated with the control module 130, or any other suitable network(s). As such, an application executing at the electronic device 180 can facilitate interaction between the user and an exercise community. In one example, the application can be configured to upload exercise-related metrics, through a network, to be shared with a community of individuals with similar fitness interests, goals, or any other suitable association with the user, and the user may be able to obtain exercise advice and/or exercise-related metrics from the community of individuals to motivate the user according to his/her goals.

In expanding upon configurations of an exercise-monitoring application being executed at the electronic device 180, the application can be configured to provide a virtual coaching environment that includes one or more of: training plans, recovery plans, information regarding competitions (e.g., training regimens configured to prepare the user for an upcoming competition), instructions for stretching, instructions for injury prevention, instructions regarding proper form for conducting an exercise, and any other suitable coaching functions. Additionally or alternatively, the application can be configured to provide alerts to the user based upon received and processed data. For instance, the application can be configured to notify the user or another entity if the user is focusing too much on a particular exercise or muscle group (e.g., by visually showing the muscle group(s) that are overemphasized and recommending other exercises to the user), or if the user is using a muscle group incorrectly during an exercise (e.g., if the user is demonstrating poor form). Additionally or alternatively, the application can provide comprehensive reports pertinent to the user's exercise behavior, including one or more of: a muscle breakdown of work performed/output for specific muscles; a breakdown of a score given for a workout, wherein the score can be tracked over time to monitor progress of the user; a classification of exercise as cardio-based or strength-based; indications of muscle atrophy, indications of rehabilitation progress; indications of fatigue; indications of potential or actual injury; and any other suitable reported factor. In one example, a report can provide a percentage of a workout associated with strength-based exercise vs. a percentage of a workout associated with cardio-based exercise. In another example, the report can additionally or alternatively provide a detailed breakdown of any exercise metric associated with one or more muscle groups, provided within a virtual display of various muscle groups. In this example, the application can be configured to accept a user input of a selection of one or more muscle groups (e.g., by selecting a portion of the virtual display of various muscle groups), and to provide relevant metrics pertaining to the muscle group(s) selected by the user.

Additionally or alternatively, the application executing at the electronic device 180 can be configured to display information directly related to muscle groups the user is monitoring, and/or to display information associated with muscle groups that the user is not actively monitoring, according to information acquired from muscle groups that the user is monitoring. As such, information from monitored muscles can be indicative of a problem elsewhere in the user's body, and monitored muscle groups can be used to provide indications or alerts pertaining to other portions of the user's body. In one example, monitored muscle groups can generate an alert that the user is positioning his bicycle seat at too high of a position, which is adversely affecting non-monitored muscle groups; in another example, monitored muscle groups can generate an alert that the user is running in a pigeon-toed manner, which is adversely affecting non-monitored muscle groups. The application(s) of the electronic device 180 can, however, be configured in any other suitable manner.

Furthermore, the system 100 can include any other suitable element(s) configured to detect and process biosignals data. Furthermore, as a person skilled in the art will recognize from the previous detailed description and from the figures and claims, modifications and changes can be made to the system 100 without departing from the scope of the system 100.

2. Method

Figure 10:
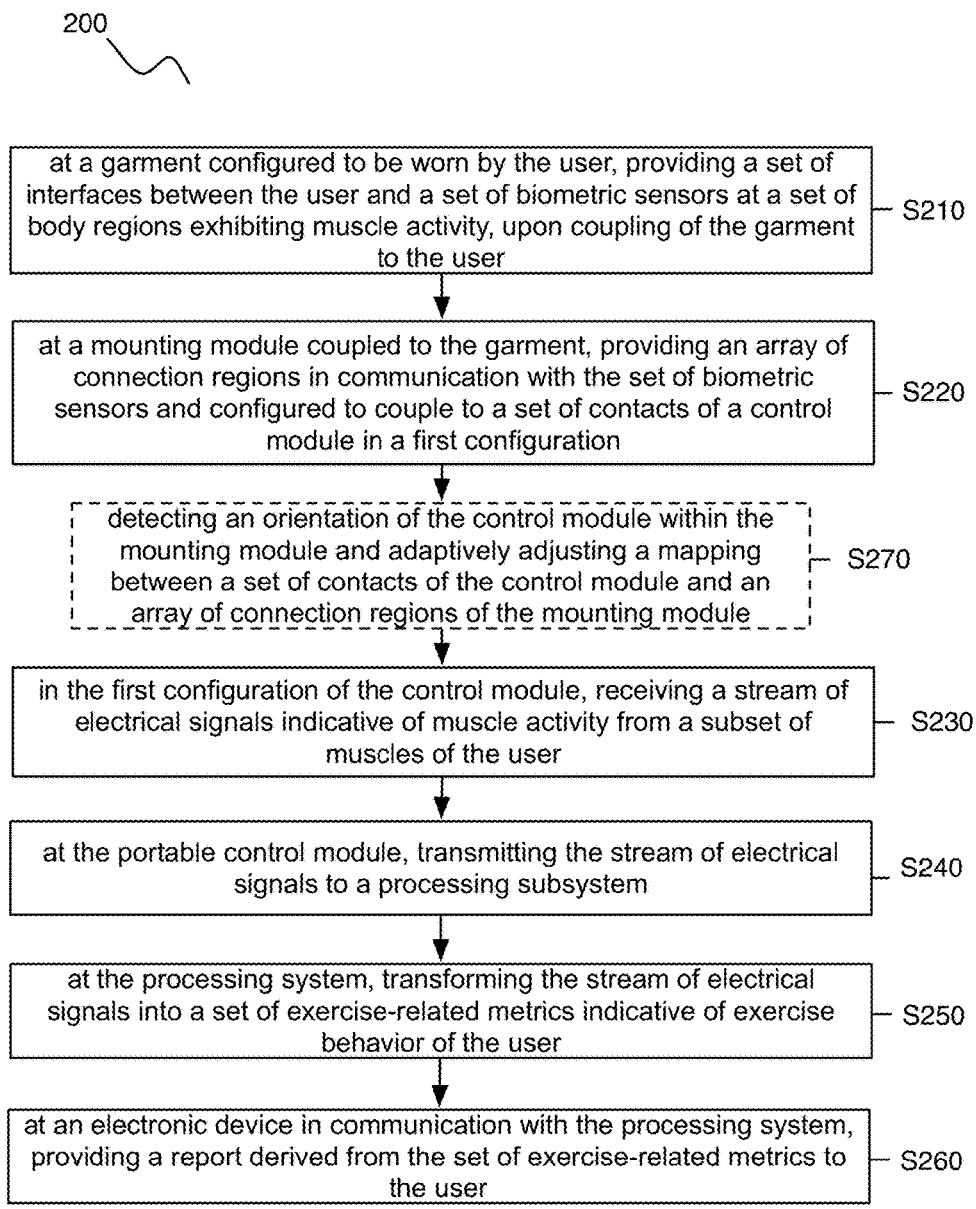
FIG. 10 depicts a flow chart of an embodiment of a method for monitoring biometric signals of a user.

As shown in FIG. 10, an embodiment of a method 200 for monitoring biometric signals of a user comprises: at a garment configured to be worn by the user, providing a set of interfaces between the user and a set of biometric sensors at a set of body regions exhibiting muscle activity, upon coupling of the garment to the user S210; at a mounting module coupled to the garment, providing an array of connection regions in communication with the set of biometric sensors and configured to couple to a set of contacts of a portable control module in a first configuration S230; at the portable control module, receiving a stream of electrical signals indicative of muscle activity from a subset of muscles of the user, in the first configuration S230; at the portable control module, transmitting the stream of electrical signals to a processing subsystem S240; at the processing subsystem, transforming the stream of electrical signals into a set of exercise-related metrics indicative of exercise behavior of the user S250; and at an electronic device in communication with the processing subsystem, providing a report derived from the set of exercise-related metrics to the user S260.

The method 200 functions to facilitate positioning of a set of biometric sensors at desired regions of a user's body, in order to detect biometric signals generated during physical activity of the user. The method 200 also functions to process detected biometric signals and to provide information derived from the processed biometric signals to the user performing a physical activity in substantially near real time, such that the user can gain insights into how to maintain or improve performance of the physical activity in a beneficial manner. In variations, the method 200 is configured to detect and process bioelectrical signals generated at a set of regions of the body of a user who is exercising (e.g., performing aerobic exercise, performing anaerobic exercise), and to present analyses in a visual manner (e.g., graphic manner, textual manner) by way of an application executing at an electronic device having a display. As such, bioelectrical signals detectable, processable, and/or analyzable according to the method 200 can include any one or more of: electromyograph (EMG) signals, electrocardiography (ECG) signals, electroencephalograph (EEG) signals, magnetoencephalograph (MEG) signals, galvanic skin response (GSR) signals, electrooculograph (EOG) signals, and any other suitable bioelectrical signal of the user. The method 200 can, however, be configured to detect, process, and/or analyze any other suitable biosignal data of the user, including one or more of: heart rate data, movement data, respiration data, location data, environmental data (e.g., temperature data, light data, etc.), and any other suitable data. The method 200 is preferably implemented at least in part at an embodiment of the system 100 described in Section 1 above; however, the method 200 can alternatively be implemented at any other suitable system for detection and processing of biometric signals from a user who is performing a physical activity.

Block S210 recites: at a garment configured to be worn by the user, providing a set of interfaces between the user and a set of biometric sensors at a set of body regions exhibiting muscle activity, upon coupling of the garment to the user. Block S210 is preferably implemented at embodiments, variations, and/or examples of the garment and the set biometric sensors described in Section 1 above; however, Block S210 can alternatively be implemented using any other suitable garment with coupled biometric sensors that are configured to detect biopotential signals indicative of muscle activity of the user. Providing the set of interfaces thus functions to provide and maintain tight coupling between sensing portions of a set of biometric sensors and desired body regions of the user as the user performs a physical activity. In providing the set of interfaces, Block S210 preferably utilizes conductive materials coupled to the garment and configured to maintain contact with the skin of the user as the user exercises; however, Block S210 can produce the set of interfaces in any other suitable manner.

In Block S210, providing the set of interfaces preferably includes generation of interfaces configured to adequately conduct one or more of: electromyography (EMG) signals, motion signals (e.g., from an accelerometer, from a gyroscope), respiration signals (e.g., respiration rate, depth of breath, thoracic variations, inspiratory flow characteristics, expiratory flow characteristics, etc.), galvanic skin response (GSR) signals, temperature-induced signals, vibration signals, bioimpedance signals, electrocardiography (ECG) signals, signals indicative of other cardiovascular parameters (e.g., pulse oximetry signals, blood pressure signals), and any other suitable type of signal. As such, the set of biometric sensors provided in Block S210 can facilitate detection of biosignals indicative of one or multiple types of biological/physiological responses to activity of a user, in providing information relevant to exercise behavior of the user.

Preferably, providing the set of interfaces in Block S210 is dependent upon the type of garment (e.g., top or bottom) provided in Block S210. Additionally, for anatomical regions having contralateral pairs, providing the set of interfaces preferably includes providing pairs of interfaces, each pair including an associated first sensor at a first body region and an associated second sensor at a second body region that is a contralateral region to the first body region. In one variation, for a garment that has a form factor of a top (e.g., shirt, tank top, etc.), the set of interfaces provided in Block S210 can include interfaces between a set of EMG electrodes and skin of the user proximal one or more of: the pectoralis muscles, the abdominal muscles, the oblique muscles, the trapezius muscles, the rhomboid muscles, the teres major muscles, the latissimus dorsi muscles, the deltoid muscles, the biceps muscles, and the triceps muscles when the garment is worn by the user. In another variation, for a garment that has a form factor of a bottom (e.g., shorts, pants, etc.), the set of interfaces provided in Block S210 can include interfaces between a set of EMG electrodes and skin of the user proximal one or more of: the gluteus maximus muscles, the gluteus medius muscles, the vastus lateralis muscles, the gracilis muscles, the semimembranosus muscles, the semitendinosis muscles, the biceps femoris, the soleus muscles, the gastrocnemius muscles, the rectus femoris muscles, the sartorius muscles, the peroneus longus muscles, and the adductor longus muscles when the garment is worn by the user. Variations of the set of interfaces provided in Block S210 can, however, be configured in any other suitable manner.

Block S220 recites: at a mounting module coupled to the garment, providing an array of connection regions in communication with the set of biometric sensors, wherein the array of connection regions is configured to couple to a set of contacts of a control module in a first configuration. Block S220 functions to enable transmission of biopotential signals generated from the body of the user, as the user exercises, from the set of sensor interfaces to a control module. Block S220 is preferably implemented at embodiments, variations, and/or examples of the garment, the control module, the mounting module, and the set biometric sensors described in Section 1 above. As such, providing the array of connection regions preferably comprises providing electrically conductive connection regions coupled between the set of biometric sensors and the mounting module in a set configuration, as described in Section 1 above, wherein a set of contacts of the control module can be coupled to the array of connection regions in a first configuration (e.g., wherein the control module is seated within the mounting module), and uncoupled from the array of connection regions in a second configuration 102 (e.g., wherein the control module is removed from the mounting module).

In variations, as discussed in relation to the control module of Section 1 above, the array of connection regions of the mounting module can be mapped to the set of contacts of the control module regardless of the orientation of the control module, such that Block S220 includes providing a symmetric array of connection regions of the mounting module, and providing a corresponding symmetric set of contacts of the control module. Furthermore, providing the array of connection regions for the control module can further include facilitating activation of indicator LEDs of the control module, wherein activation of the indicator LEDs can be triggered upon proper coupling between the array of connection regions of the mounting module and the set of contacts of the control module. While Block S220 is preferably described in relation to the system described in Section 1 above, Block S220 can alternatively be implemented using any other suitable garment with coupled biometric sensors configured to communicate with a control module.

Block S230 recites: in the first configuration of the control module, receiving a stream of electrical signals indicative of muscle activity from a subset of muscles of the user. Block S230 functions to acquire biosignal data from the user by way of the set of biometric sensors, when the control module is coupled with the garment in the first configuration. Block S230 preferably includes receiving signals from paired sensor channels (e.g., associated with paired biometric sensors of the set of biometric sensors). As such, paired biometric sensors and contacts of the set of contacts of the control module can facilitate reception of signals that can be used to determine a signal differential (i.e., a biopotential difference) across a pair of associated sensor channels.

Receiving the stream of electrical signals in Block S230 can include conditioning the stream of electrical signals S235 at a signal conditioning module, such as the signal conditioning module described in Section 1 above, in order to generate a conditioned signal stream. In conditioning the stream of electrical signals, Block S235 can include passing the stream of electrical signals through at least one of a low pass filter, a high pass filter, a band-pass filter, and a notch filter (i.e., a band-stop filter), in order to preprocess the datasets to remove a portion of any artifacts or interference (e.g., due to noise). In variations, the low pass filter can function to remove higher frequency noise and the high pass filter can function to remove lower frequency noise (e.g., due to waist movement/pressure artifacts). Any of the filters can further be supplemented with filters configured to remove or mitigate the frequency spectrum of any known noise components. Additionally or alternatively, Block S235 can include any one or more of: smoothing, clipping, deconvolving, detrending/offsetting, standardizing, resampling, hard-binding, predicting, windowing, and performing any other suitable data conditioning process upon any signals received in Block S230. In variations, S230 can further include storing conditioned or unconditioned signal data in memory, as describe in relation to the memory of the electronics subsystem in Section 1 above.

Block S240 recites: at the portable control module, transmitting the stream of electrical signals to a processing subsystem, which functions to transmit conditioned and/or unconditioned data derived from the stream of signals for additional processing. Block S240 is preferably implemented at an embodiment, variation, or example of the communication interface(s) described in relation to the electronics subsystem of the control module described in Section 1 above, whereby signal transmission is performed over a network associated with the control module and the processing subsystem. Transmitting the stream of electrical signals in Block S240 can be performed substantially continuously (e.g., every second, every millisecond, etc.) and/or in near-real-time, thereby facilitating near-real-time provision of comprehensive feedback to the user. Alternatively, transmitting the stream of electrical signals in Block S240 can be performed intermittently (e.g., only when the control module is coupled to the garment, at random time points, etc.) and/or in non-real-time. Furthermore, according to variations of the communication interface described in Section 1 above, transmitting the signals in Block S240 can involve wireless and/or wired transmission of data derived from the stream of electrical signals to the processing subsystem.

Block S250 recites: at the processing subsystem, transforming the stream of electrical signals into a set of exercise-related metrics indicative of exercise behavior of the user. Block S250 functions to generate an analysis derived from the stream of electrical signals received in Block S240, which can be used to provide feedback to the user regarding aspects of his/her exercise behavior. Block S250 can include determining metrics including one or more of: a metric related to effort output (e.g., total effort output as a ratio between an amount of work performed by a muscle group and a maximum amount of work that can be performed by the muscle group), a metric derived from an amount of cardio-activity performed by the user, a metric derived from an amount of strength-based activity performed by the user, a metric related to balance in utilization of all muscles of a muscle group; a metric related to a total number of muscles/muscle groups utilized during one or more exercises, a metric related to a number of repetitions of a performed exercise, a metric related to a number of sets of a performed exercise, a metric related to a distance conquered or time duration of an exercise, a metric associated with improperness or properness of form in performing one or more exercises (e.g., as identified by signals of the signal stream indicative of muscles the user is using to perform an exercise, in relation to a desired group of muscles the user should use to perform the exercise with proper form), a metric related to target intensity level (e.g., as determined using a target intensity level desired by the user or another entity associated with the user, in relation to actual intensity level indicated by signals of the signal stream), a metric related to average heart rate throughout a workout, a metric related to average heart rate throughout a portion of a workout, a breakdown of muscle exertion for different muscle groups, exercise progress-related metrics, and any other suitable metrics. In generating any one or more of the above metrics, the processing system can be configured to utilize time information and signal feature information (e.g., amplitude, frequency, signal signatures, etc.) in determining metrics associated with individual muscles, groups of muscles, and overall assessments of activity of the user.

Figure 11A:
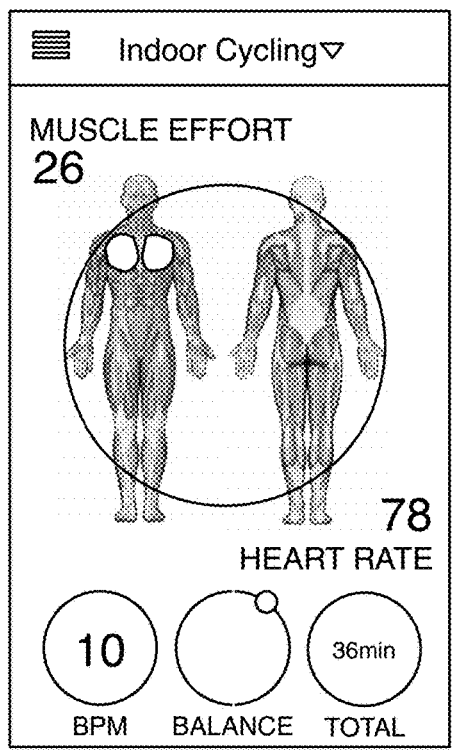
FIGS. 11A-11B depict examples of portions of an exercise-monitoring application in a method and/or system for monitoring biometric signals of a user.

Block S260 recites: at an electronic device in communication with the processing subsystem, providing a report derived from the set of exercise-related metrics to the user. Block S260 preferably involves processing of the set of exercise-related metrics into a report that provides insights to the user, pertaining to the user's exercise behavior. Block S260 preferably implements an embodiment, variation, or example of the processing subsystem, electronic device, and network described in Section 1 above; however, Block S260 can additionally or alternatively be implemented using any other suitable processing and information provision elements. In providing the report(s), Block S260 preferably utilizes an exercise-monitoring application being executed at the electronic device, an example of which is shown in FIG. 11A. The report(s) can contribute to a virtual coaching environment that includes one or more of: training plans, recovery plans, information regarding competitions (e.g., training regimens configured to prepare the user for an upcoming competition), instructions for stretching, instructions for injury prevention, instructions regarding proper form for conducting an exercise, and any other suitable coaching functions derived from metrics associated with the user's muscular activity.

Figure 11B:
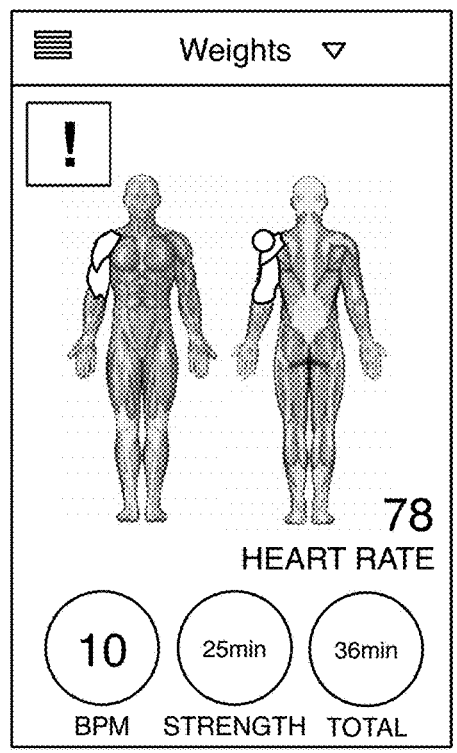

Additionally or alternatively, the report(s) provided in Block S260 can be used to provide alerts to the user based upon received and processed data, an example of which is shown in FIG. 11B. For instance, Block S260 can include notifying the user or another entity if the user is focusing too much on a particular exercise or muscle group (e.g., by visually showing the muscle group(s) that are overemphasized and recommending other exercises to the user), or if the user is using a muscle group incorrectly during an exercise (e.g., if the user is demonstrating poor form). Additionally or alternatively, the reports can provide synopses pertaining to one or more of: a muscle breakdown of work performed/output for specific muscles; a breakdown of a score given for a workout, wherein the score can be tracked over time to monitor progress of the user; a classification of exercise as cardio-based or strength-based; indications of muscle atrophy, indications of rehabilitation progress; indications of fatigue; indications of potential or actual injury; and any other suitable reported factor. In one example, a report can provide a percentage of a workout associated with strength-based exercise vs. a percentage of a workout associated with cardio-based exercise. In another example, the report provided in Block S260 can additionally or alternatively provide a detailed breakdown of any exercise metric associated with one or more muscle groups, provided within a virtual display of various muscle groups.

The method 200 can further include Block S270, as shown in FIG. 10, which recites: detecting an orientation of the control module within the mounting module and adaptively adjusting a mapping between a set of contacts of the control module and an array of connection regions of the mounting module. Block S270 functions to enable proper signal reception and processing from a symmetric control module that can be coupled to the garment in multiple orientations. Block S270 can implement contact configuration(s) of the set of contacts of the control module and any other suitable data (e.g., accelerometer data, gyroscope data) in order to detect the orientation of the control module relative to the garment. Once the orientation of the control module is detected, Block S270 can include adapting signal reception and processing functions accordingly. As such, Block S270 can allow the control module to operate properly regardless of how the control module is coupled with the garment, in receiving and processing signals from the set of biometric sensors. For example, using the contact configuration shown in FIG. 6, signals X and Y can be received by way of contacts 1A and 1B in a first orientation of the control module, but if the control module is positioned "upside-down" in a second orientation, firmware implementing Block S270 can adapt signal reception and processing of the control module to receive signals X and Y by way of contacts 14B and 14A, respectively. As such, in the example, Block S270 can facilitate dynamic modification of the contact mapping in order to property attribute signals X and Y to the correct muscle group or set of biometric sensors.

Additionally or alternatively, Block S270 can include post-processing of signals based upon supplementary data that can allow signatures associated with one or muscle groups or types of activity to be identified. For instance, if accelerometer data indicates motion behavior associated with a first muscle group, but EMG signal data indicates muscle activity not associated with the first muscle group, Block S270 can involve reconfiguring a mapping between the set of contacts of the control module and the set of biometric sensors, post-reception of the signal stream from the set of biometric sensors, and generating metrics and reports according to the reconfigured mapping. Any other signatures derived from one or more of: gyroscope data, accelerometer data, GPS data, temperature data, location data, heart rate data, and any other suitable data can be used to identify the most probable muscle groups being used in an activity, and adjusting a mapping between the set of contacts of the control module accordingly. As such, identification of the configuration of the control module relative to the garment can be facilitated based upon cross-correlation between different types of data (e.g., accelerometer data, EMG sensor data), detection of identification contact configurations, and/or in any other suitable manner.

The method 200 can further include any one or more of: detecting misalignment of the control module, providing an indication of misalignment of the control module (e.g., using indicator LEDs), receiving a user input and providing a customized report based upon the user input (e.g., allowing the user to select a portion of a virtual display of various muscle groups and providing a report based upon the selection), allowing the user to receive information and feedback (e.g., training information, motivational feedback) from a community of associated users, and any other suitable steps or blocks that promote proper exercise behavior of the user.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for monitoring biometric signals of a user comprising:
    a garment configured to be worn by the user and comprising a mounting module having an array of connection regions;
    a set of biometric sensors coupled to the garment, the set of biometric sensors configured to communicate with the array of connection regions and configured to receive and transmit biometric signals of the user by way of the array of connection regions; and
    a portable control module configured to couple to the garment in a first configuration and to decouple from the garment in a second configuration and comprising:
        a housing comprising a first surface and a second surface, the first surface including an array of openings through the first surface, the housing including a first waterproof seal between the first surface and the second surface;
        a set of contacts coupled to the housing and extending through the array of openings, each contact in the set of contacts coupling to at least one of the array of connection regions in the first configuration, the set of contacts composed of a conductive polymer material and forming waterproof seals at corresponding openings of the array of openings; and
        an electronics subsystem coupled to the housing and in communication with a second region of each of the set of contacts.

2. The system of claim 1, further comprising a processing subsystem configured to:

receive and process the biometric signals from the set of biometric sensors;

determine a set of exercise-related metrics associated with muscle activity of the user based upon the biometric signals; and provide a report to the user based upon at least a subset of the set of exercise-related metrics.

3. The system of claim 2, wherein the set of biometric sensors comprises paired sensors configured to enable detection of a biopotential difference across the paired sensors, and wherein the processing subsystem is configured to determine at least one of the set of exercise-related metrics based upon the biopotential difference.

4. The system of claim 1, wherein the set of contacts of the portable control module is configured in a symmetric array having a shared axis of symmetry with the housing of the portable control module, the symmetric array including a plurality of rows of contacts and a plurality of columns of contacts.

5. The system of claim 4, wherein the portable control module is configured to be coupled with the mounting module in a first rotated orientation and a second rotated orientation, the second rotated orientation configured 180 degrees from the first rotated orientation, wherein the array of connection regions is a rectangular array of connection regions, and wherein the portable control module comprises a processor and associated firmware configured to adaptively adjust a plurality of mappings between the set of contacts and the rectangular array of connection regions of the mounting module upon detection that the portable control module is in one of the first rotated orientation and the second rotated orientation, a first mapping of the plurality of mappings associated with a pair of contacts of the set of contacts.

6. The system of claim 5, wherein the set of contacts of the portable control module is arranged such that paired sensors of the set of biometric sensors are configured to electrically couple to the pair of contacts of the set of contacts.

7. The system of claim 5, wherein the first pair of contacts is configured for detection of biopotential difference, the plurality of mappings further including:

a second mapping associated with a second pair of contacts of the set of contacts, the second pair of contacts configured for applying a voltage differential across the second pair of contacts; and a third mapping associated with a third pair of contacts of the set of contacts, the third pair of contacts configured for identification of the mounting module corresponding to the garment.

8. The system of claim 7, wherein the first pair of contacts is positioned at opposing corners of the symmetric array, wherein the second pair of contacts is positioned at a first pair of diagonally opposing locations within the symmetric array and the third pair of contacts is positioned at a second pair of diagonally opposing positions within the symmetric array.

9. The system of claim 1, wherein the mounting module includes a set of layers coupled to the garment and configured to provide a biasing force that maintains contact between the set of contacts of the portable control module and the array of connection regions of the mounting module in the first configuration.

10. The system of claim 9, wherein the set of layers of the mounting modules includes:

a fabric layer affixed to the garment and defining a receiving pocket for the portable control module, wherein the fabric layer has an elastic opening that accommodates reception of the portable control module;

a cradle deeper than the fabric layer and comprising the array of connection regions that couple to the set of biometric sensors; and a foam ring at least partially surrounding the cradle and deeper than the fabric layer.

11. The system of claim 10, wherein each connection region in the array of connection regions has a first portion that is exposed through a first cradle surface, configured to provide a waterpoof seal at the first cradle surface, and configured to contact the connection region of at least one contact of the portable control module, and wherein each connection region in the array of connection regions has a second portion in communication with the first portion and configured to couple to a lead proximal a second cradle surface, wherein the lead enables electrical communication between a connection region of the array of connection regions and at least one biometric sensor of the set of biometric sensors.

12. The system of claim 1, wherein the electronics subsystem is coupled to a set of indicator LEDs configured to indicate alignment of the portable control module with the mounting module in the first configuration.

13. The system of claim 1, wherein the mounting module is configured to secure the portable control module in the first configuration such that the set of contacts compressibly abuts the array of connective regions.

14. The system of claim 1, wherein the portable control module does not provide power to the garment.

15. The system of claim 1, wherein each biometric sensor comprises a conductive polymer screened onto a layer of the garment.

16. A garment for wearing by a user, comprising:

a mounting module having an array of connective regions, the mounting module configured to secure and communicatively couple to a removable control module comprising a first surface and a second surface of a housing, the removable control module including a first waterproof seal between the first surface and the second surface, the first surface including an array of openings through the first surface, the removable control module further comprising a set of contacts coupled to the housing and extending through the array of openings, the set of contacts configured to align with and abut the array of connective regions when the mounting module secures the removable control module, and the set of contacts of the removable control module composed of a conductive polymer material and forming waterproof seals at corresponding openings of the array of openings; and a set of biometric sensors coupled to the garment, the set of biometric sensors configured to communicate with the array of connective regions, each biometric sensor communicatively coupled to a corresponding region in the array of connective regions and configured to detect muscle activity and, in response, transmit biometric signals representative of the detected muscle activity to the corresponding region and to a contact of the set of contacts that abuts the corresponding region.

17. The garment of claim 16, wherein the removable control module is configured to couple to a processing subsystem configured to:

receive and process the biometric signals from the set of biometric sensors upon detecting signals corresponding to a set of muscle groups associated with diagonally-opposing pairs of the set of contacts and;
determine a set of exercise-related metrics associated with muscle activity of individual muscle groups of the set of muscle groups of the user based upon the biometric signals; and
visually render, at a display device in communication with the processing subsystem, a report to the user based upon at least a subset of the set of exercise-related metrics, with representation of individual muscle groups of the set of muscle groups.

18. The garment of claim 17, wherein the set of biometric sensors comprises paired sensors configured to detect a biopotential difference across the paired sensors, and wherein the processing subsystem is configured to determine at least one of the set of exercise-related metrics based upon the biopotential difference.

19. The garment of claim 16, wherein the mounting module is configured to apply a securing force onto the removable control module when the removable control module is secured within the mounting module, the securing force causing the set of contacts to forcibly compress into the array of connective regions.

20. A system for monitoring biometric signals of a user comprising:
a garment configured to be worn by the user and comprising a mounting module having an array of connective regions;
a set of biometric sensors coupled to the garment, the set of biometric sensors configured to communicate with the array of connective regions, each biometric sensor communicatively coupled to a connective region of the array of connective regions and configured to detect muscle activity and, in response, transmit biometric signals representative of the detected muscle activity to the corresponding region; and
a removable control module comprising a first surface and a second surface of a housing, the removable control module including a first waterproof seal between the first surface and the second surface, the first surface including an array of openings through the first surface, the removable control module configured to couple to the mounting module in a first orientation and in a second orientation, the removable control module further comprising:
a set of contacts coupled to the housing and extending through the array of openings, the set of contacts configured to align with and abut the array of connective regions when the removable control module is secured by the mounting module, the set of contacts of the removable control module composed of a conductive polymer material and forming waterproof seals at corresponding openings of the array of openings, the removable control module configured comprising a processor and associated firmware operable to map each contact of the set of contacts to a corresponding connective region based on whether the removable control module is coupled to the mounting module in the first orientation or the second orientation.

21. The system of claim 20, wherein the removable control module is configured to couple to a processing subsystem configured to:
receive and process the biometric signals from the set of biometric sensors to determine a set of exercise-related metrics associated with muscle activity of the user based upon the biometric signals; and
provide a report to the user based upon at least a subset of the set of exercise-related metrics.

22. The system of claim 20, wherein the set of biometric sensors comprises paired sensors configured to detect a biopotential difference across the paired sensors, and wherein the processing subsystem is configured to determine at least one of the set of exercise-related metrics based upon the biopotential difference.

23. The system of claim 20, wherein the mounting module is configured to apply a securing force onto the removable control module when the removable control module is secured within the mounting module, the securing force causing the set of contacts to forcibly compress into the array of connective regions.

* * * * *